(12) United States Patent
Brosch et al.

(10) Patent No.: US 7,112,196 B2
(45) Date of Patent: Sep. 26, 2006

(54) MULTI-ELEMENT ARRAY FOR ACOUSTIC ABLATION

(75) Inventors: Jared Brosch, Cicero, IN (US); Andreas Hadjicostis, Carmel, IN (US)

(73) Assignee: Piezo Technologies, Inc., Indianapolis, IN (US)

( * ) Notice: Subject to any disclaimer, the term of this patent is extended or adjusted under 35 U.S.C. 154(b) by 290 days.

(21) Appl. No.: 10/686,119

(22) Filed: Oct. 15, 2003

(65) Prior Publication Data

US 2004/0254569 A1 Dec. 16, 2004

Related U.S. Application Data

(60) Provisional application No. 60/478,649, filed on Jun. 13, 2003.

(51) Int. Cl.
*A61B 18/18* (2006.01)

(52) U.S. Cl. .......................................... 606/27; 606/28

(58) Field of Classification Search ............ 606/27–52, 606/32, 34, 41; 601/2; 600/437, 439; 607/99
See application file for complete search history.

(56) References Cited

U.S. PATENT DOCUMENTS

| | | | |
|---|---|---|---|
| 5,091,893 A * | 2/1992 | Smith et al. ............... | 367/153 |
| 5,176,142 A | 1/1993 | Mason | |
| 5,323,781 A | 6/1994 | Ideker et al. | |
| 5,412,854 A | 5/1995 | Lockwood et al. | |
| 5,456,259 A | 10/1995 | Barlow et al. | |
| 5,590,657 A | 1/1997 | Cain et al. | |
| 5,630,837 A * | 5/1997 | Crowley ........................ | 601/2 |
| 5,951,304 A | 9/1999 | Wildes et al. | |
| 6,117,101 A | 9/2000 | Diederich et al. | |
| 6,206,831 B1 * | 3/2001 | Suorsa et al. ............... | 600/439 |
| 6,245,064 B1 | 6/2001 | Lesh et al. | |
| 6,254,599 B1 | 7/2001 | Lesh et al. | |
| 6,392,330 B1 | 5/2002 | Zloter et al. | |
| 6,488,630 B1 | 12/2002 | Hand et al. | |
| 6,497,667 B1 | 12/2002 | Miller et al. | |
| 6,500,174 B1 | 12/2002 | Maguire et al. | |
| 6,508,775 B1 | 1/2003 | McKenzie et al. | |
| 6,514,249 B1 | 2/2003 | Maguire et al. | |
| 6,527,769 B1 | 3/2003 | Langberg et al. | |
| 2002/0062079 A1 | 5/2002 | Tahara | |
| 2002/0089262 A1 | 7/2002 | Topa et al. | |
| 2002/0175591 A1 | 11/2002 | Schreiner et al. | |
| 2003/0013968 A1 | 1/2003 | Fjield et al. | |

* cited by examiner

*Primary Examiner*—Roy D. Gibson
*Assistant Examiner*—Pete Vrettakos
(74) *Attorney, Agent, or Firm*—Woodard, Emhardt, Moriarty, McNett & Henry LLP

(57) ABSTRACT

A tissue ablation apparatus is disclosed that includes an elongate, flexible device operable to be percutaneously place in vasculature of a patient. The device has an array of 8 or more tissue ablation elements carried on a flexible circuit substrate located at a distal end portion. A cable is also included that has a number of electrical conductors insulated from one another that are each electrically coupled to a different one of the elements. One or more connectors are electrically coupled to the cabling at a proximal end portion of the device.

11 Claims, 15 Drawing Sheets

MULTI-ELEMENT ARRAY FOR ACOUSTIC ABLATION

CROSS-REFERENCE TO RELATED APPLICATIONS

The present application claims the benefit of U.S. Provisional Patent Application No. 60/478,649 filed Jun. 13, 2003, which is hereby incorporated by reference. The present application is related to the commonly owned U.S. Patent Application entitled: "MINIATURE ULTRASONIC PHASED ARRAY FOR INTRACARDIAC AND INTRACAVITY APPLICATIONS" invented by Brosch et al. and filed on even date herewith, and the commonly owned U.S. Patent Application entitled: "COMPOSITIONS FOR HIGH POWER PIEZOELECTRIC CERAMICS" invented by Liufu and filed on even date herewith, all of which are hereby incorporated by reference.

BACKGROUND

The present invention relates to acoustic energy generation, and more particularly, but not exclusively, relates to the fabrication, use, and structure of devices including an array of elements to generate ultrasonic energy for tissue ablation.

Cardiac arrhythmia, and atrial fibrillation in particular, persist as common and dangerous medical aliments associated with abnormal cardiac chamber wall tissue, and are often observed in elderly patients. In patients with cardiac arrhythmia, abnormal regions of cardiac tissue do not follow the synchronous beating cycle associated with normally conductive tissue in patients with sinus rhythm. Instead, the abnormal regions of tissue aberrantly conduct to adjacent tissues, disrupting the cardiac cycle into an asynchronous rhythm. Such abnormal conduction is known to occur at various regions of the heart.

Irregular cardiac function and corresponding hemodynamic abnormalities caused by atrial fibrillation can result in stroke, heart failure, and other medical problems. Indeed, atrial fibrillation is believed to be a significant cause of cerebral stroke. Specifically, it is theorized that the hemodynamic irregularity resulting from fibrillatory wall motion precipitates thrombus formation within the atrial chamber. A thromboembolism is ultimately dislodged into the left ventricle which thereafter pumps the embolism into the cerebral circulation that can result in a stroke. Accordingly, numerous procedures for treating atrial arrhythmia have been developed, including pharmacological, surgical, and catheter ablation procedures.

Among these, the less invasive catheter-based approaches have generally been targeted to atrial segmentation with ablation catheter devices adapted to form linear or curvilinear lesions in the wall tissue which defines the atrial chambers. Other disclosed approaches provide shaped or steerable guiding sheaves for the purpose of directing tip-ablation catheters toward the posterior left atrial wall such that sequential ablations along the predetermined path of tissue may create the desired lesion. In other approaches, atrial fibrillation is addressed with an ablation device that navigates through the circulatory system to form one or more circumferential lesions in pulmonary vein tissue. Various energy delivery modalities have been disclosed for forming lesions, including use of microwave, laser, thermal conduction, ultrasound, and more commonly radio frequency energies to create conduction blocks. U.S. Pat. Nos. 6,117,101; 6,245,064 B1; 6,254,599 B1; 6,600,174 B1; 6,608,775 B2; 6,514,249 B1; and 6,527,769 B2 provide additional background information concerning various cardiac ablation devices.

Frequently, these and other approaches do not provide a desired degree of control with respect to the targeting of ablation energy on tissue. Furthermore, for ultrasonic generating devices directed to circumferential tissue ablation, the level of power needed to ablate the surrounding tissue can result in heat dissipation problems and/or fracture of ultrasound-generating elements. Thus, there is an ongoing demand for further contributions in this area of technology. Moreover, advances in this area of technology can have application in noncardiac medical treatments and/or in nonmedical procedures.

SUMMARY

One embodiment of the present invention is a unique acoustic ablation technique. Other embodiments include unique methods, systems, devices, and apparatus for generating acoustic energy. As used herein, "ultrasound" and "ultrasonic" refer to acoustic energy waveforms having a frequency of more than 20,000 Hertz (Hz) through one or more media at standard temperature and pressure.

A further embodiment of the present invention includes: providing a therapeutic device including an array of elements that each produce acoustic energy when activated, positioning the therapeutic device within a patient's body, and ablating tissue by activating one or more of the elements while the device is within the patient's body. In one form, the array elements are carried on a flexible circuit substrate and are composed of a piezoelectric material suitable to produce ultrasonic energy. For one particular variation of this form, each element produces a maximum acoustic power output of at least one quarter of a watt at a frequency of several megahertz, although other variations may have a different power level and/or frequency range.

Another embodiment includes: providing a therapeutic device with ultrasonic ablation elements fixed in relation to one another and a circumference of the device, positioning the device within a patient's body, and activating different groups of the elements while the device is in the patient's body to correspondingly provide ultrasonic energy focused to ablate different tissue regions.

In still another embodiment, a system includes an ablation device and a control station. The ablation device is operable to be percutaneously placed within a patient's body, and includes a proximal end portion, a distal end portion, and an array of ultrasonic ablation elements located at the distal end portion. These elements may be carried on a flexible substrate. The proximal end portion of the device is coupled to the control station. The control station includes one or more processors operable to selectively activate one or more elements of the array. In one form, operating logic for the station is provided as processor programming instructions stored in memory that is selectively accessed by the one or more processors. In a particular form, these instructions are stored on a removable memory device such as a floppy disk, CD or DVD. The ablation device can include cabling that couples the array to the control station and includes a number of electrical conductors each electrically insulated from one another and each being electrically connected to a different one of the elements. For such forms, the control station can selectively change the focus of ultrasonic energy emanating from the device to ablate different tissue regions while the device is in the patient's body. In one particular arrangement, the control station activates different subsets of the elements in a desired sequence to correspondingly focus ultrasonic energy on different tissue segments circumferentially surrounding the device.

In yet another embodiment, an assembly is provided that includes a rigid piezoelectric member mounted to a flexible circuit substrate. The piezoelectric member is divided into a number of pieces to provide an array of ultrasonic ablation elements, and the flexible circuit substrate is coupled to cabling and the cabling to a connector. The connector includes a number of electrical contacts each insulated from one another and each being electrically connected to a different one of the elements.

A further embodiment includes an apparatus encoded with programming instructions executable by one or more processors to activate different subsets of ultrasonic ablation elements included in an ablation element array in accordance with predefined sequence. For each stage in the sequence, the subset of elements collectively focuses ultrasonic energy on a different circumferential segment of tissue surrounding the array to form a tissue lesion. The apparatus can be in the form of memory storing the instructions, including, but not limited to, a removable memory device, such as a floppy disk, CD, or DVD.

One object of the present invention is to provide a unique ultrasonic ablation technique.

Another object of the present invention is to provide a unique method, system, device, or apparatus for generating acoustic energy.

Further forms, objects, features, aspects, benefits, advantages, and embodiments of the present invention shall become apparent from the detailed description and drawings provided herewith.

DETAILED DESCRIPTION OF SELECTED EMBODIMENTS

Figure 1:
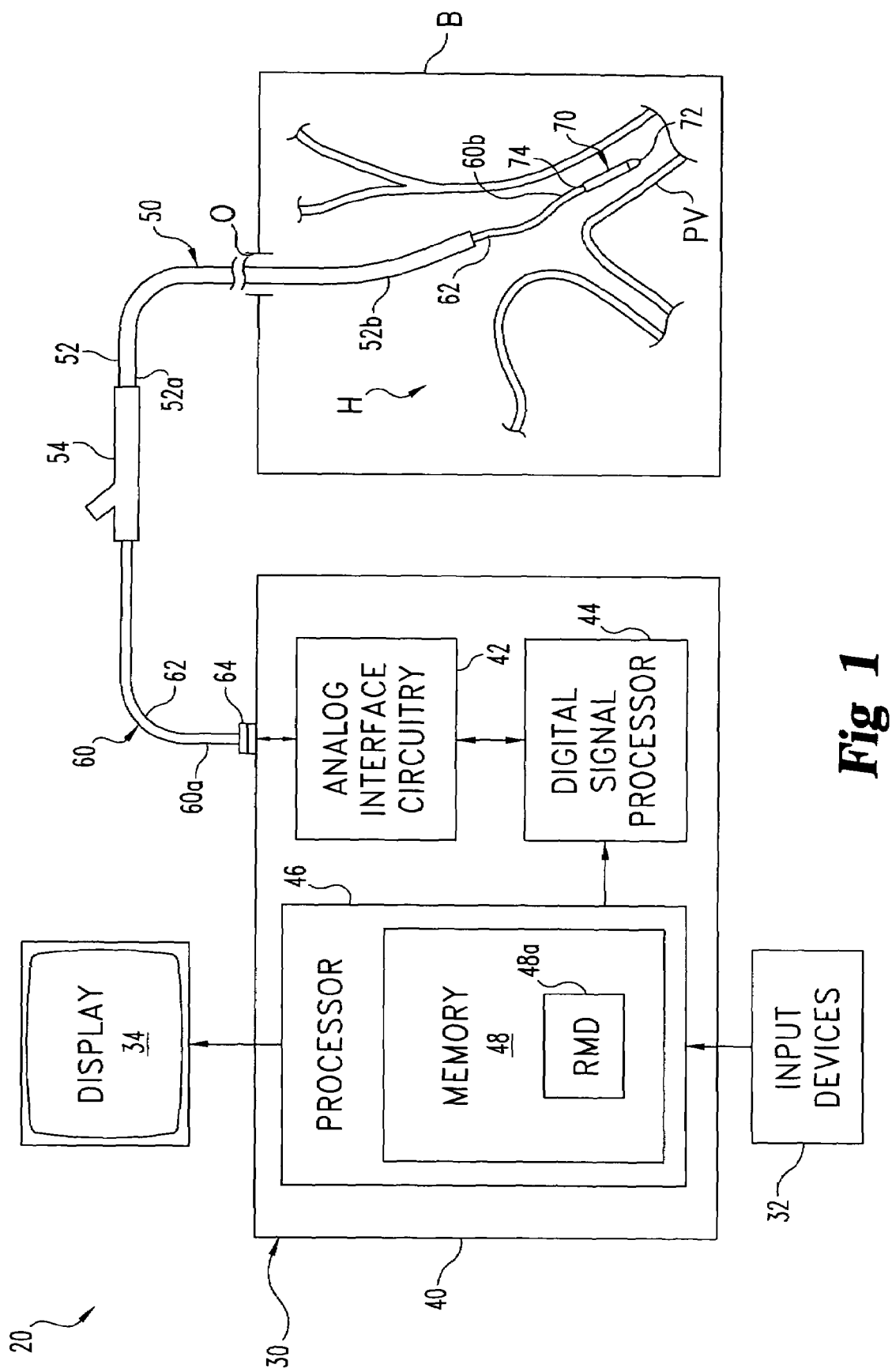
FIG. 1 is a schematic view of a system to provide medical treatment.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

One embodiment of the present invention includes an ultrasonic device structured for percutaneous insertion in the human body. The device includes an array of piezoelectric elements located at a distal end portion, and cabling connected to the array that extends from the array to a proximal end portion of the device. The elements are carried on a flexible circuit substrate including at least two levels of electrical conductor patterns. The cabling includes multiple conductors each electrically insulated from one another and each electrically connected to a different one of the elements. In one preferred form, the elements number at least eight. In a more preferred form, the elements number at least 32. In a still more preferred form, the elements number at least 64 and are configured to ablate tissue when activated by an appropriate electrical stimulus through the cabling.

FIG. 1 illustrates system 20 that includes an ablation array and associated equipment arranged to provide medical treatment. System 20 includes control station 30, catheterization equipment 50, and ablation device 60. Ablation device 60 is coupled to control station 30 and configured with catheterization equipment 50 for placement within body B of a human patient, as schematically represented in FIG. 1. Station 30 includes operator input devices 32 and operator display device 34. Input devices 32 include an alphanumeric keyboard and mouse or other pointing device of a standard variety. Alternatively or additionally, one or more other input devices can be utilized, such as a voice input subsystem or a different type as would occur to those skilled in the art. Operator display device 34 can be of a Cathode Ray Tube (CRT) type, Liquid Crystal Display (LCD) type, plasma type, Organic Light Emitting Diode (OLED) type, or such different type as would occur to those skilled in the art. Alternatively or additionally, one or more other operator output devices can be utilized, such as a printer, video recorder, mass data storage device, one or more loudspeakers, headphones, or such different type as would occur to those skilled in the art. Station 30 also can include one or more communication interfaces suitable for connection to a computer network, such as a Local Area Network (LAN), Municipal Area Network (MAN), and/or Wide Area Network (WAN) like the internet; a medical diagnostic device; another therapeutic device; a medical imaging device; a Personal Digital Assistant (PDA) device; a digital still image or video camera; and/or audio device, to name only a few.

Station 30 also includes processing subsystem 40 for processing signals and data associated with system 20. Subsystem 40 includes analog interface circuitry 42, Digital Signal Processor (DSP) 44, data processor 46, and memory 48. Analog interface circuitry 42 is responsive to control signals from DSP 44 to provide corresponding analog stimulus signals to ablation device 60. At least one of analog circuitry 42 and DSP 44 includes one or more digital-to-analog converters (DAC) to facilitate operation of system 20 in the manner to be described in greater detail hereinafter.

Processor 46 is coupled to DSP 44 to bidirectionally communicate therewith, selectively provide output to display device 34, and selectively respond to input from operator input devices 32.

DSP 44 and/or processor 46 can be of a programmable type; a dedicated, hardwired state machine; or a combination of these. DSP 44 and processor 46 perform in accordance with operating logic that can be defined by software programming instructions, firmware, dedicated hardware, a combination of these, or in a different manner as would occur to those skilled in the art. For a programmable form of DSP 44 or processor 46, at least a portion of this operating logic can be defined by instructions stored in memory 48. Programming of DSP 44 and/or processor 46 can be of a standard, static type; an adaptive type provided by neural networking, expert-assisted learning, fuzzy logic, or the like; or a combination of these.

Memory 48 is illustrated in association with processor 46; however, memory 48 can be separate from or at least partially included in one or more of DSP 44 and processor 46. Memory 48 includes at least one Removable Memory Device (RMD) 48a. Memory 48 can be of a solid-state variety, electromagnetic variety, optical variety, or a combination of these forms. Furthermore, memory 48 and can be volatile, nonvolatile, or a mixture of these types. Memory 48 can be at least partially integrated with circuitry 42, DSP 44, and/or processor 46. RMD 48a can be a floppy disc, cartridge, or tape form of removable electromagnetic recording media; an optical disc, such as a CD or DVD type; an electrically reprogrammable solid-state type of nonvolatile memory, and/or such different variety as would occur to those skilled in the art. In still other embodiments, RMD 48a is absent.

Circuitry 42, DSP 44, and processor 46 can be comprised of one or more components of any type suitable to operate as described herein. Further, it should be appreciated that all or any portion of circuitry 42, DSP 44, and processor 46 can be integrated together in a common device, and/or provided as multiple processing units. For a multiple processing unit form of DSP 44 or processor 46; distributed, pipelined, and/or parallel processing can be utilized as appropriate. In one embodiment, circuitry 42 is provided as one or more components coupled to a dedicated integrated circuit form of DSP 44; processor 46 is provided in the form of one or more general purpose central processing units that interface with DSP 44 over a standard bus connection; and memory 48 includes dedicated memory circuitry integrated within DSP 44 and processor 46, and one or more external memory components including a removable disk form of RMD 48a. Circuitry 42, DSP 44, and/or processor 46 can include one or more signal filters, limiters, oscillators, format converters (such as DACs or digital-to-analog converters), power supplies, or other signal operators or conditioners as appropriate to operate system 20 in the manner to be described in greater detail hereinafter.

Equipment 50 includes flexible catheter 52 with proximal end 52a opposite distal end 52b, and catheter port device 54. Proximal end 52a is connected to catheter port device 54 to be in fluid communication therewith. Catheter 52 includes one or more lumens extending therethrough. Equipment 50 is introduced into and removed from body B through opening O in a standard manner that typically includes one or more other components not shown to enhance clarity.

Ablation device 60 has proximal end portion 60a and distal end portion 60b. Ablation device 60 includes electrical cabling 62 with connector 64 electrically connected to station 30. Cabling 62 extends from connector 64 at proximal end portion 60a through port device 54 and a lumen of catheter 52 to distal end portion 60b. Ablation device 60 includes ultrasound ablation array assembly 70 and terminates at distal device tip 72. Assembly 70 is connected to cabling 62 at distal end portion 60b by interface 74.

Figure 2:
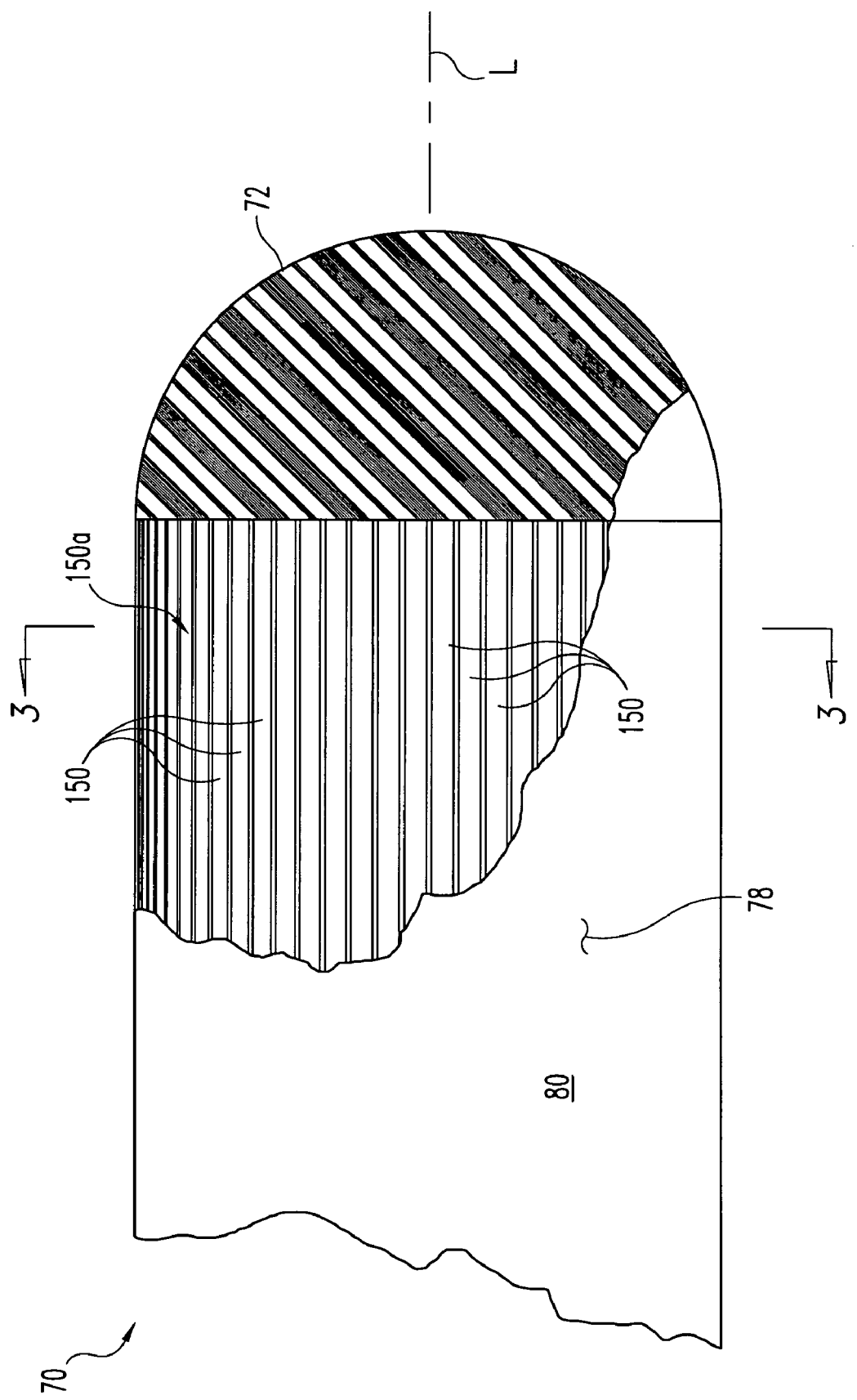
FIG. 2 is a partial, cut-away view of an ablation device included in the system of FIG. 1.
Figure 3:
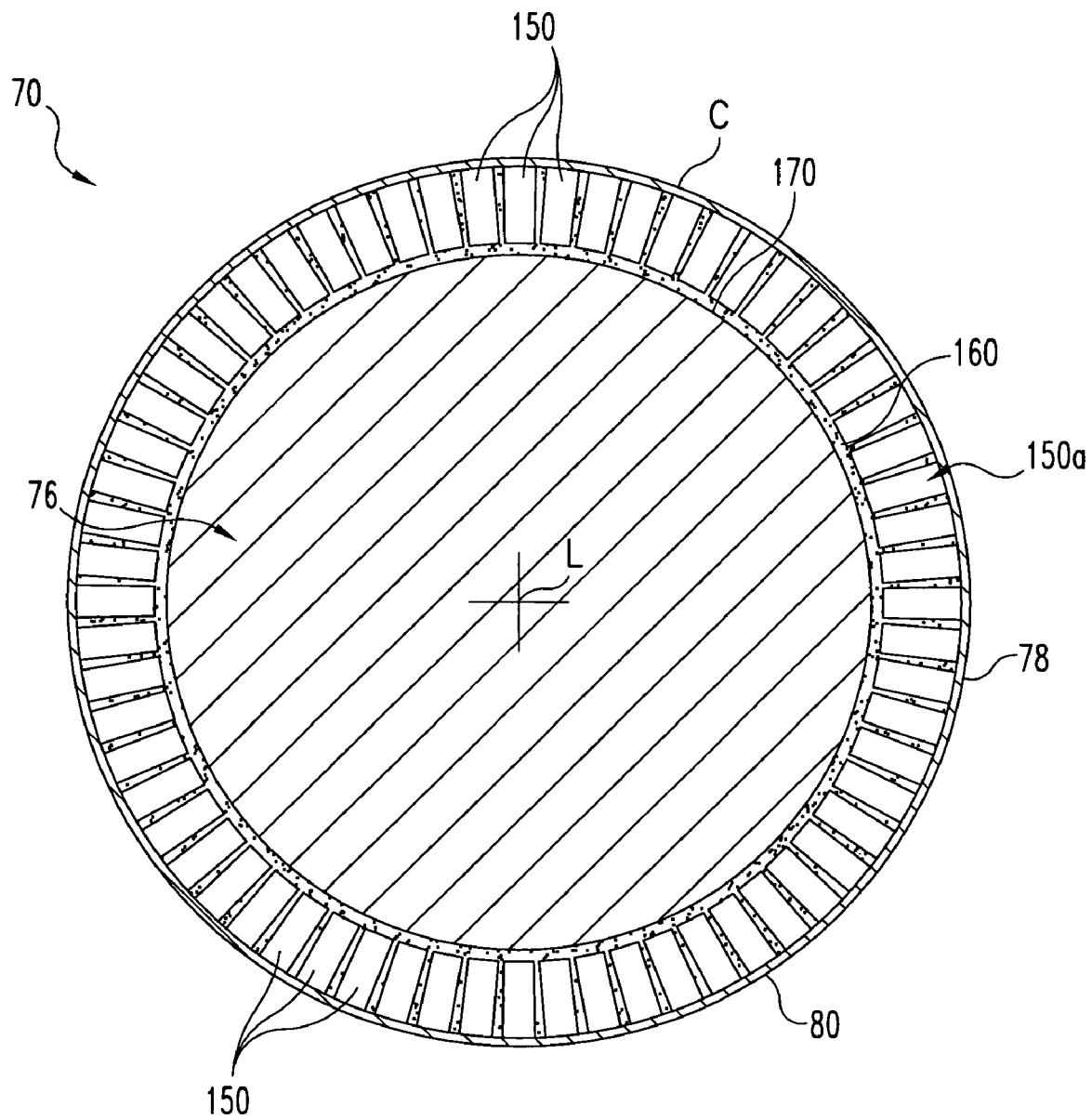
FIG. 3 is a cross-sectional view of the ablation device of FIG. 2 corresponding to section line 3—3.

Further aspects of assembly 70 are illustrated in the partial cut-away, side view of FIG. 2 and the cross-sectional view of FIG. 3. Assembly 70 extends along longitudinal centerline axis L and includes flexible circuit substrate 80 carrying array 150a. Substrate 80 and array 150a are shaped generally in the form of a right circular cylinder in FIGS. 2 and 3. Array 150a includes a number of piezoelectric ablation elements 150 positioned in interior 76 under an outer surface 78 of assembly 70. Elements 150 are each made of a piezoelectric material that responds to an appropriate electrical stimulus to generate acoustic energy in the ultrasonic frequency range. Elements 150 are each generally rigid relative to substrate 80 and are elongate with a longitude generally parallel to axis L. Elements 150 are each generally sized and shaped the same, and are evenly spaced apart from one another. As more specifically shown in FIG. 2, tip 72 is made of an elastomeric material that abuts the distal end of substrate 80 and array 150.

Referring specifically to FIG. 3, centerline axis L is generally perpendicular to the view plane and is accordingly represented by cross-hairs that intersect at the origin of the circular, cross sectional circumference C of device 60 at assembly 70. Correspondingly, axis L is centrally located relative to array 150a in FIGS. 2 and 3. Elements 150 are generally equidistant from axis L, being spaced approximately evenly thereabout and also being evenly spaced along circumference C. In a preferred embodiment of the present application, elements 150 number eight or more. In a more preferred embodiment, elements 150 number 16 or more. In another more preferred embodiment, elements 150 number 24 or more. In an even more preferred embodiment, elements 150 number 32 or more. In a still even more preferred embodiment, elements 150 number 64 or more as illustrated in FIG. 3. Elements 150 can each be made of the same piezoelectric material. Alternatively, one or more elements 150 can be made of material different than one or more other of elements 150.

Assembly 70 includes a filling/adhesive material 160 between adjacent elements 150 and cylindrical backing rod member 170 in interior 76. In one embodiment, material 160 is a standard epoxy and member 170 is formed from a thermoplastic and/or thermoset polymeric resin selected to minimize transmission of ultrasonic energy from array 150a therethrough. In another embodiment, the same composition is used for both material 160 and member 170. In still other embodiments, one or more other materials or backing structures are used in interior 76 of assembly 70 between elements 150 as would occur to those skilled in the art.

Referring generally to FIGS. 1–5, one mode of operating system 20 is next described. Using a standard catheterization procedure, catheter 52 is inserted through opening O into the vasculature of body B and directed into heart H. This procedure can include utilization of a guide wire that is then subsequently removed. The distal end 52b of catheter 52 is positioned along a desired region of pulmonary vein PV.

After placement of catheter 52, ablation device 60 is inserted through port device 54 and a lumen of catheter 52 and is slidingly advanced towards distal end 52b. Advancement of distal end portion 60b continues in this manner until assembly 70 emerges from distal end 52b and reaches a desired position within pulmonary vein PV. During these operations, one or more standard imaging devices can be utilized to visualize the position of catheter 52 and assembly 70. For materials used in equipment 50 or device 60 that are transparent or translucent to a selected imaging technique (such as polymeric resins that are generally transparent to x-ray based imaging), a marker that is opaque to such imaging technique can be included in catheter 52 and/or assembly 70 to aid with visualization. In one embodiment, distal end portion 60b of device 60 is sized to readily slide through a 7-French catheter (2 millimeter outer diameter) positioned in heart H of body B in such a manner. Device 60 can optionally include one or more position sensing devices of the type described, for example, in U.S. Pat. No. 6,514,249 B1 to Maguire et al. In one particular form of this option, one or more of elements 150 are utilized to sense position of assembly 70 relative to surrounding tissue of body B.

After positioning, array 150a of device 60 is controllably activated with station 30 to selectively ablate tissue by application of acoustic power from one or more of elements 150 in the ultrasonic range. For one preferred form, each element 150 is operable to output a maximum acoustic power of at least about 0.25 watt. In a more preferred form, each element 150 is operable to output a maximum acoustic power of 2 watts or more.

Figure 4:
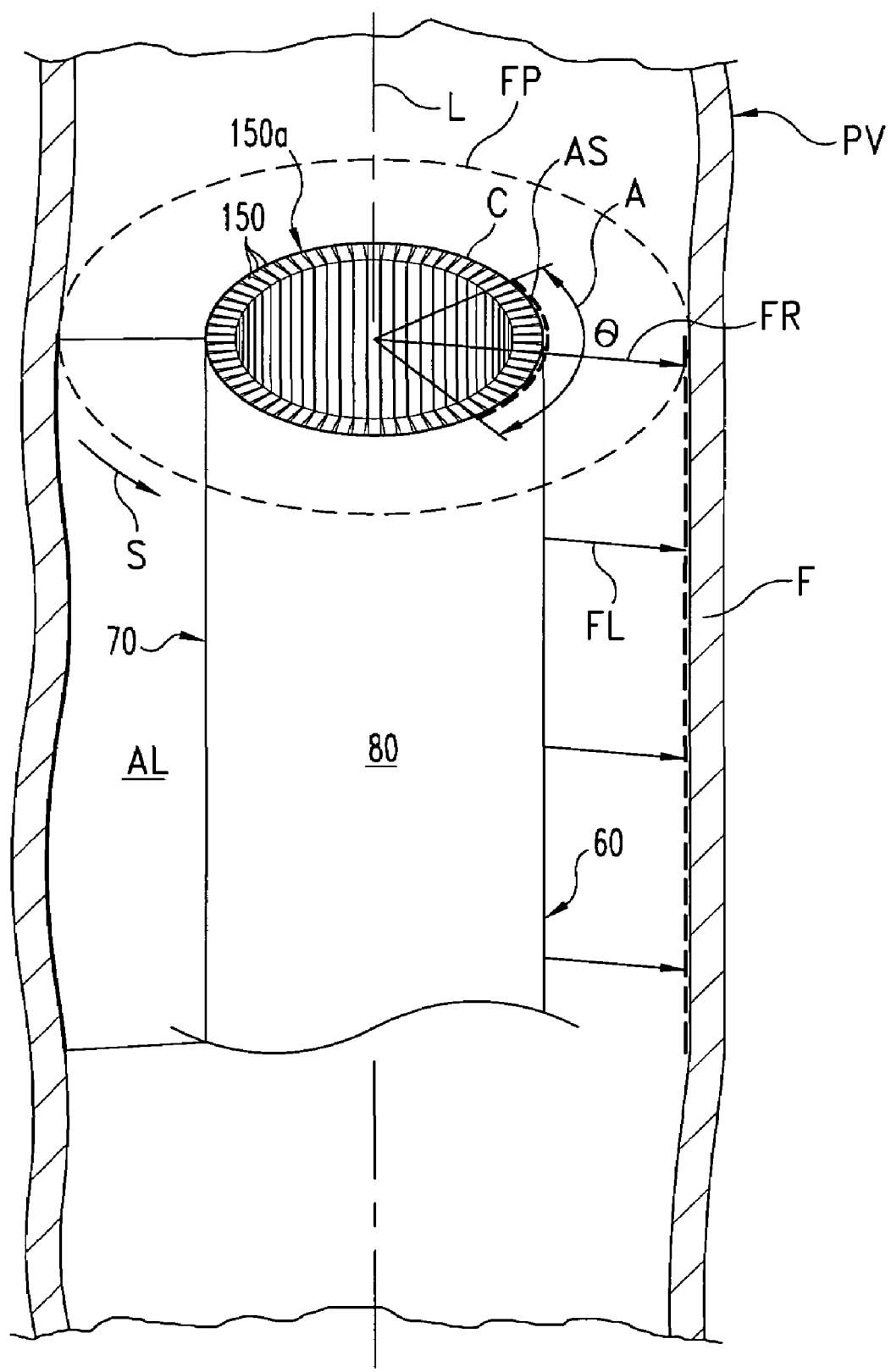
FIG. 4 is a schematic representation of an array of the ablation device shown in FIGS. 1–3 in a blood vessel.

In FIG. 4, array 150a of assembly 70 is schematically shown with tip 72 removed to more specifically show the spatial relationship of elements 150 with respect to tissue of pulmonary vein PV. In one mode of operation, different subsets of elements 150 are activated in a selected sequence in accordance with operating logic of subsystem 40 of station 30. In one preferred embodiment, sixteen consecutive elements 150 are activated at one time corresponding to a 90 degree or less angular aperture A as shown in FIG. 4. The activation stimulus for each element 150 of a given subset is a 7.5 Megahertz (MHz) sinusoidal electrical signal received via cabling 62 in this embodiment. By controlling relative phase and magnitude of the oscillatory electrical stimulus to each of the activated elements, a relatively narrowly focused region of ultrasonic acoustic power can be concentrated on a tissue region of pulmonary vein PV. In FIG. 4, this focal region F is represented by a like-labeled broken line segment with focal length FL along focal axis FR represented by a radial ray. In one implementation, different subsets of sixteen elements 150 are sequentially activated to advance focal region F along focal perimeter FP shown in FIG. 4, forming a ring-shaped ablation legion in the circumferentially surrounding tissue of pulmonary vein PV. Elements 150 of a given sixteen element subset correspond to an arc segment AS along circumference C. Accordingly, activated elements 150 of a subset are consecutively positioned with each being immediately next to at least one other activated subset element 150 and no unactivated elements 150 positioned between activated elements 150 in the subset segment AS. As element 150 is activated at one end of segment AS, element 150 at the other end of segment as is deactivated, providing a new, overlapping subset of active elements 150 that includes 15 elements 150 of the prior subset. In this manner, the subsets change in sequence one element at a time at uniform time intervals until a circumferential lesion is formed. A schematically represented portion of such an ablation lesion is labeled AL in FIG. 4. The rotational progression of focused ultrasonic energy about axis L, and correspondingly the formation of lesion AL, is represented by the counter-clockwise direction of rotation shown with sweep arrow S. Formation of lesion Al is provided in this manner to reduce, if not eliminate, atrial fibrillation and related heart arrhythmia by disrupting atrial node signaling. Typically, a ring-shaped type of lesion in the circumferentially surrounding tissue of pulmonary vein PV is desired.

For this specific embodiment, circuitry 42 can include a DSP-controllable function generator that provides an oscillatory electrical input to a phase shift stage. This phase shift stage includes a number of active, all-pass filters adjusted to provide different phase outputs in relation to one another, where the number of outputs desired corresponds to the number of differently phased elements 150 in an activated subset. For one form, eight differently phased outputs are provided—one for every two elements 150 of a sixteen member subset to provide symmetry about the focal axis FR. The phase-shifted signals are provided to DSP-controlled preamplifiers in a subsequent preamplification stage to account for any gain/loss changes that may have occurred during the all-pass filtering in the phase shift stage. The outputs of the preamplifiers are provided to high-frequency amplifiers in a subsequent amplification stage to amplify the signals from the preamplifiers by a fixed amount of gain. The final output gain can be controlled with the function generator and/or preamplifiers. To provide for sequential activation of different subsets, the outputs of the amplifiers can be coupled to different elements 150 by way of one or more DSP-controlled switching matrices or trees included in circuitry 42.

In other embodiments, circuitry 42 can be differently configured, including arrangements to select between different subset quantities, relative phase relationships, amplification, and the like. In alternative forms, the activation pattern can sweep clockwise and/or include a different number of subset elements. In still other embodiments, the subset element quantity may vary from one subset to the next, subsets may be sequenced in a pattern that lacks a rotational progression, subsets may be constituted of nonconsecutive elements 150 (such that one or more elements are skipped or activated out of consecutive order), more than one element 150 may be activated or deactivated at the same time, a change from one activated subset to another activated subset may not include any of the same elements 150, and/or elements 150 may be active only one at a time. Additionally or alternatively, system 20 can be used to provide ablation treatment for other medical conditions and/or other types of tissue. For any of these variations, subsystem 40 can be correspondingly configured.

In further embodiments directed to ablation of tissues by navigation through the circulatory system and/or other body passageways, device 60 can be arranged with a longitudinal channel or passage to receive a guide wire. Guide wire placement is typically performed in advance of catheter 52. With an appropriate guide wire passageway, device 60 can be slidably advanced along a previously placed guide wire with or without utilization of catheter 52. Alternatively or additionally, device 60 can be of a self-directing, steerable variety that does not require a catheter or guide wire to navigate body passageways to a target site within the patient.

Figure 5:
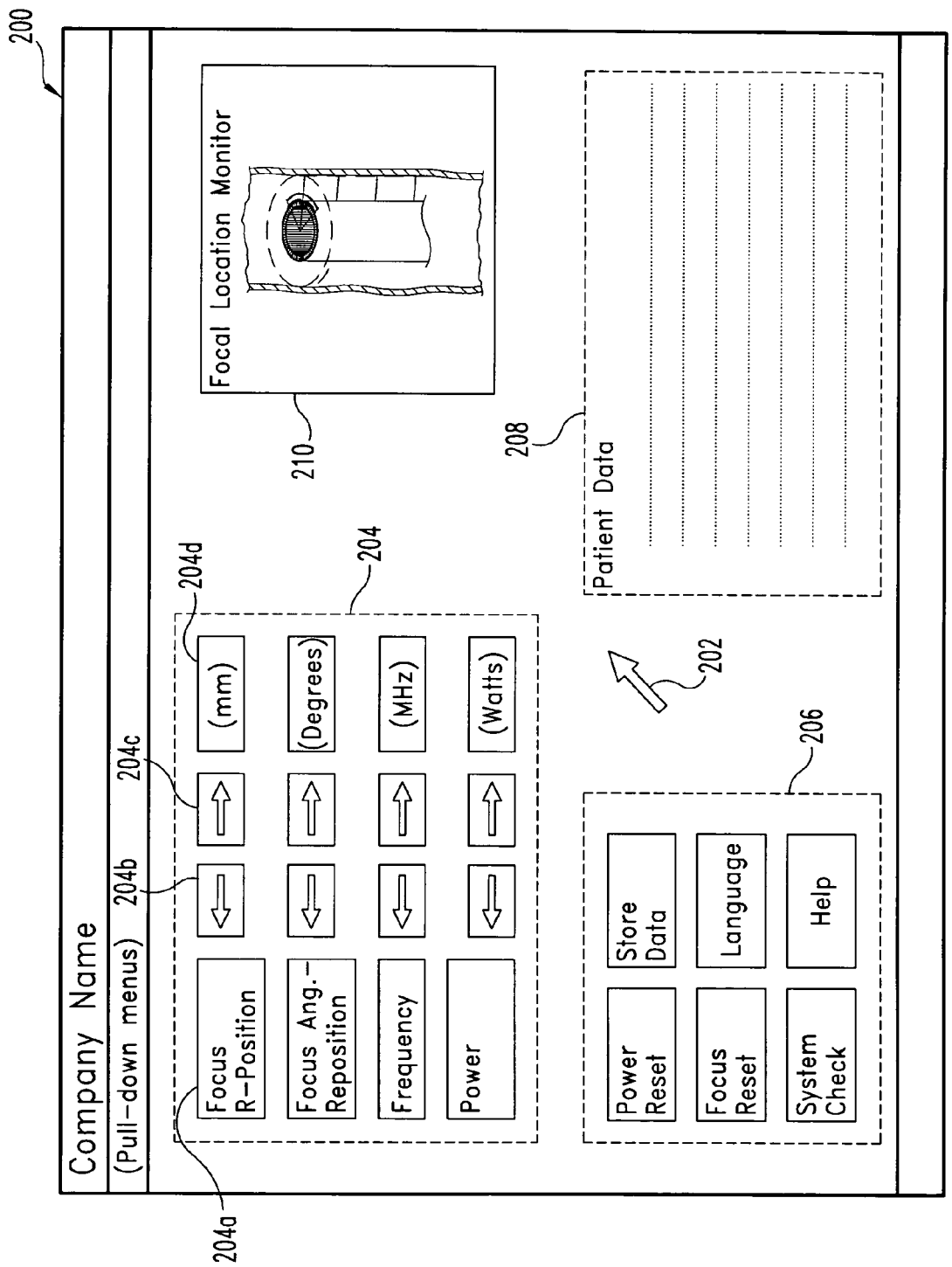
FIG. 5 is a diagram of an operator interface that can be utilized with the system of FIG. 1.

Referring additionally to FIG. 5, one form of operator display interface 200 is shown. Interface 200 includes input device pointer 202 that can be moved to different Graphical User Interface (GUI) buttons, windows, pull-down menus, data entry fields, and the like. Ablation control region 204 of interface 200 includes four columns 204a, 204b, 204c, and 204d. Column 204a provides labels corresponding to different properties of ablation device operation. Specifically, the label in the top row of column 204a indicates the radial focal length FL along axis FR and correspondingly the radius of focal perimeter FP. The label in the second row of column 204a indicates relative angular position and/or angular aperture size of the active group of one or more elements. The label in the third row of column 204a indicates the frequency of the oscillatory electrical stimulation signal being provided to active elements 150 of array 150a. In one form, system 20 provides for an ultrasonic frequency range from about 3 to about 15 megahertz, although other frequencies outside this range can be utilized in different embodiments. The label in the fourth row of column 204a indicates the power level of the activated group of one or more elements 150.

Column 204b icons of region 204 can be selected with pointer 202 to decrease the property indicated by the column 204a label in the same row. Column 204c icons can be selected with pointer 202 to increase the property indicated by the column 204a label in the same row. Column 204d displays the current value of the property indicated by the column 204a label in the same row, showing the units of the corresponding property in parentheses. It should be understood that in other arrangements, different frequencies and/or different power levels may be applied among different elements 150 at the same time. Alternatively or additionally, more than one element or group of elements may be activated at the same time corresponding to different relative positions and optionally different focal lengths. The arrangement of region 204 can be readily adjusted to account for such variations if desired.

System control region 206 includes buttons that can be selected with pointer 202 to cause the action indicated by the corresponding label. Data field 208 provides multiple lines of alphanumeric text regarding the patient undergoing the procedure. Region 210 provides a visual representation of array 150a relative to the surrounding tissue of pulmonary vein PV. In one form, some or all of region 210 is a window that shows an image of distal end portion 60b during use with or without overlays corresponding to focal information and active elements. Such an image can be provided from imaging equipment coupled to or integrated in station 30. Station 30 can be arranged to show other information under control of the operator and further includes a control (such as one or more buttons or the like) for an operator to direct the activation of elements 150 in accordance with a given sequence and/or to step through different activation sequence steps. Further, station 30 can include limits on its operation to prevent improper use and/or can monitor one or more physiological aspects of the patient to accordingly adjust operation with or without operator intervention.

Figure 6:
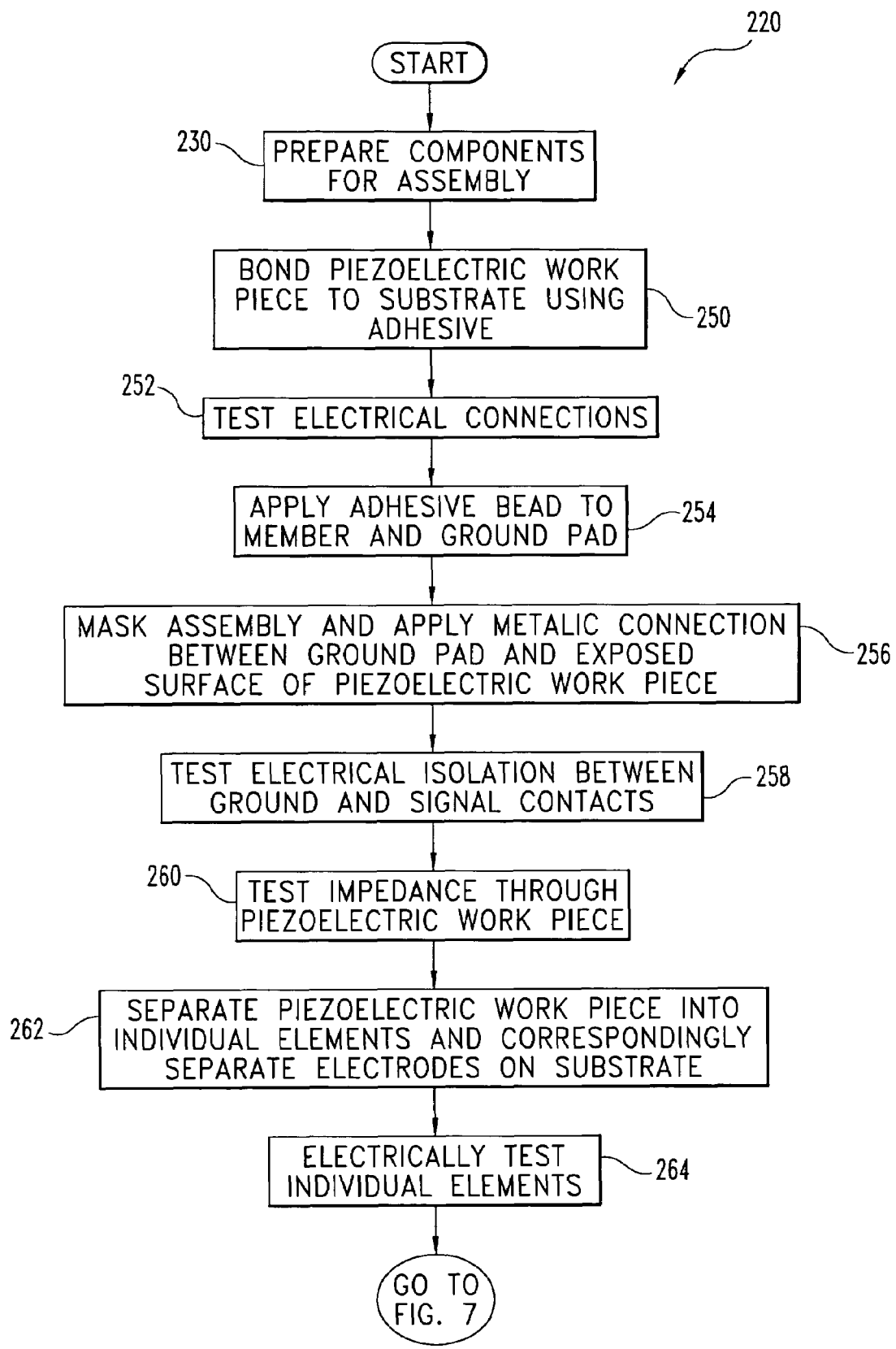
FIGS. 6 and 7 provide a flowchart illustrating one process for manufacturing the ablation device included in the system of FIG. 1.
Figure 7:
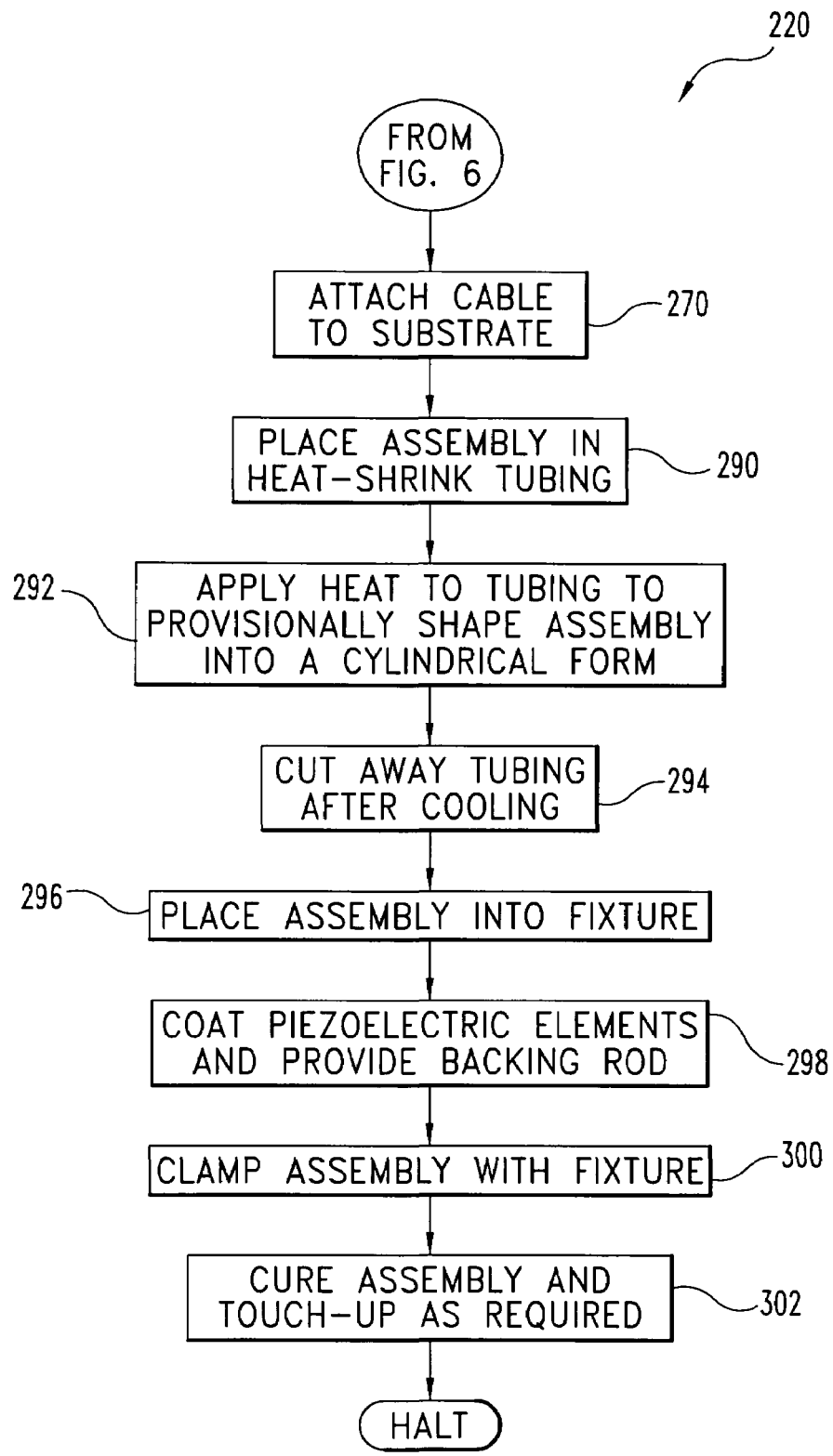
Figure 8:
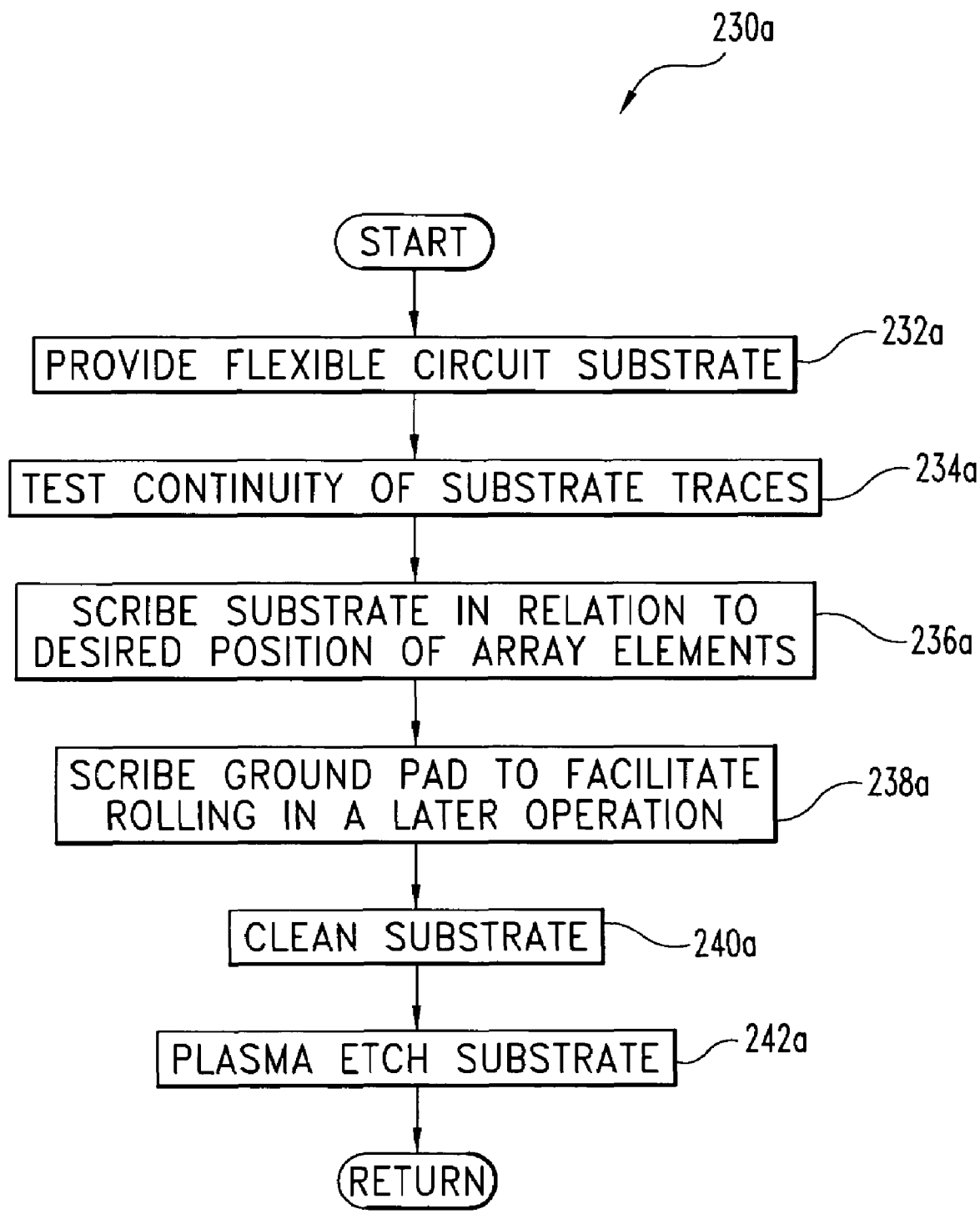
FIG. 8 is a flowchart illustrating the preparation of a flexible circuit substrate for the process of FIGS. 6 and 7.
Figure 11:
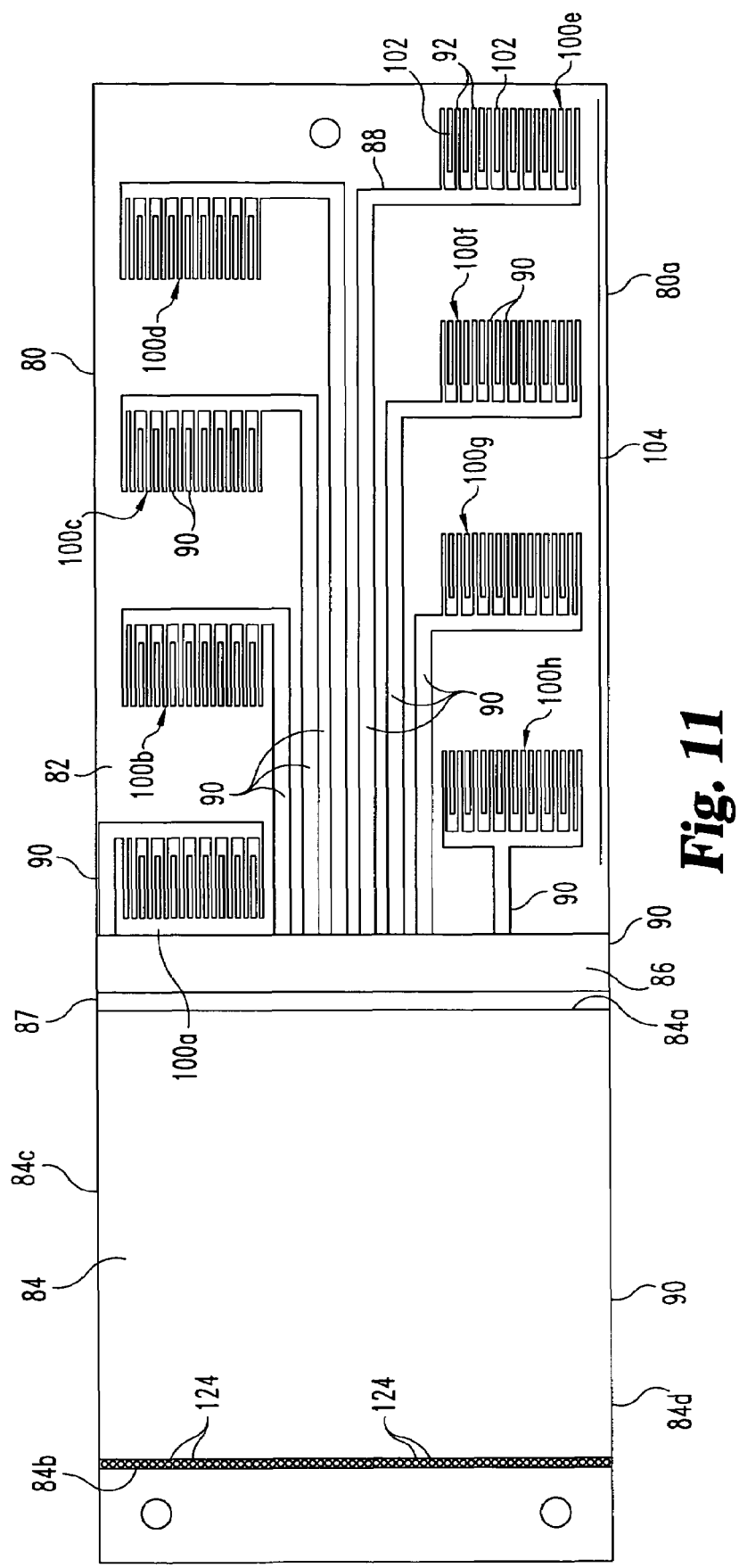
FIG. 11 is a plan view of one side of a flexible circuit substrate for assembly of the ablation device in accordance with the process of FIGS. 6 and 7.
Figure 12:
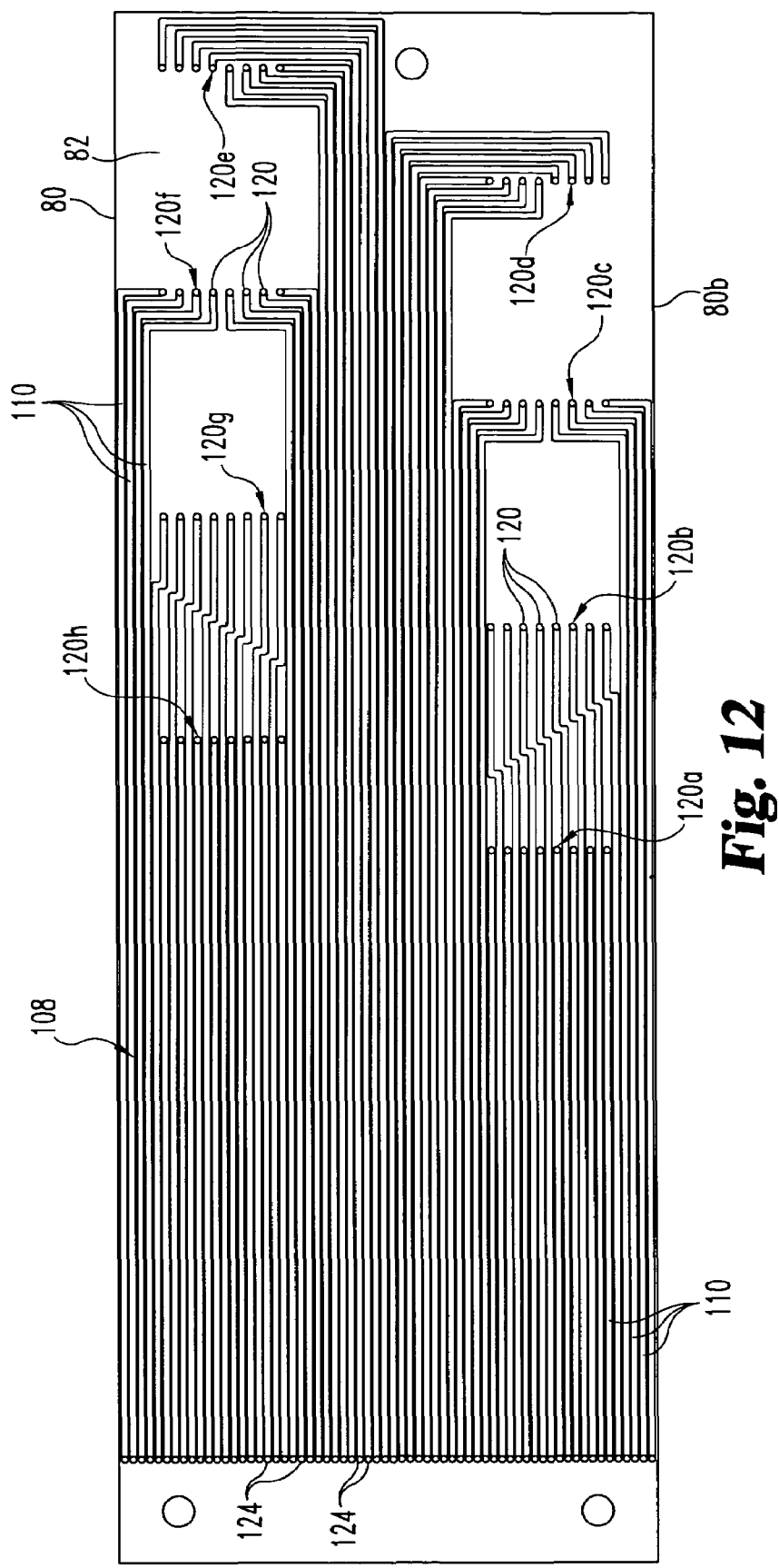
FIG. 12 is a plan view of another side of the flexible circuit substrate shown in FIG. 11.

Turning next to the flowchart of FIGS. 6–7, one procedure for the manufacture of ablation device 60 is described as process 220. Process 220 begins with the preparation of parts in operation 230. Referring to the flowchart of FIG. 8, procedure 230a is described in which substrate 80 is prepared in accordance with operation 230. Procedure 230a begins with the provision of substrate 80 in component form prior to assembly with array 150a. FIGS. 11 and 12 further illustrate substrate 80 in this form, showing opposing sides 80a and 80b, respectively. Substrate 80 is of a flexible circuit type with sides 80a and 80b being separated from one another by layer 82 formed of an electrically nonconductive material.

Side 80a of FIG. 11 includes electrical conductors 90. Conductors 90 include array mounting pad 84 electrically isolated at edge 84a from ground pad 86 by insulating region 87. Conductors 90 also include trace pattern 88 electrically connected to ground pad 86. Pattern 88 extends from ground pad 86 to ground pads 92. Conductors 90 also include contact pad sets 100a, 100b, 100c, 100d, 100e, 100f, 100g, and 100h (collectively designated pad sets 100). Each pad set 100 includes ten ground pads 92 and eight signal pads 102. Only a few individual conductors 90, pads 92, and pads 102 are designated by reference numerals to preserve clarity. Each of pads 102 is partially surrounded by corresponding pairs of ground pads 92 and electrically isolated therefrom to enhance signal noise reduction. Side 80a also includes an alignment trace 104 used in subsequent operations of process 220.

Side 80b of FIG. 12, includes trace pattern 108 of electrical conductors 110. Conductors 110 are connected to electrically conductive through-hole via sets 120a, 120b, 120c, 120d, 120e, 120f, 120g, 120h (collectively designated signal pad vias 120). In the right-side region of FIG. 12, conductors 110 are electrically connected to corresponding vias 120. Vias 120 of each of sets 120a–120h are electrically connected to signal pads 102 of sets 100a–100h, respectively, as described in connection with side 80a. In the left-side region of FIG. 12, conductors 110 are connected to electrically conductive through-hole vias 124. Vias 124 electrically connect to pad 84 near edge 84b. Vias 120 and 124 extend through corresponding holes in layer 82 of substrate 80 to provide the respective electrical connections to pads 102 and 84. Only a few of conductors 110, vias 120, and vias 124 are designated by reference numerals to preserve clarity.

In this component form of substrate 80, pads 84, 86, 92, and 102 are provided in the form of exposed metallization. Typically, this metallization includes a noble metal such as copper, gold, platinum, or silver or an alloy thereof, that is plated and/or tinned to facilitate soldering. Generally, patterns 88 and 108, including vias 120 and 124 on side 80b are otherwise covered by an electrically nonconductive material. This material is typically in the form of a film or coating of a translucent or transparent polymeric resin, but can be comprised of one or more different materials as would occur to those skilled in the art. Alternatively some or all of such patterns may not be covered by an insulating material at this stage.

Returning to FIG. 8, procedure 230a continues with operation 234a. In operation 234a, electrical continuity of the substrate traces is tested in a standard manner. After this testing, procedure 230a proceeds to operation 236a. In operation 236a, pad 84 is scribed with a dicing saw through the corresponding metallization utilizing trace 104 for alignment. Cuts are made generally parallel to one another and edges 84c and 84d. Cuts are generally located in the longitudinal center of the footprint to be occupied by each corresponding element 150 in assembly 70. In operation 238a, ground pad 86 is scribed to facilitate bending of substrate 80 in a subsequent operation of process 220. From operation 238a, procedure 230a continues with operation 240a in which substrate 80 is cleaned. In one form, this cleaning includes a methanol alcohol wipe. In operation 242a, component preparation concludes with a two to three minute treatment of substrate 80 in a plasma-etching device. Procedure 230a then returns to process 220.

Figure 9:
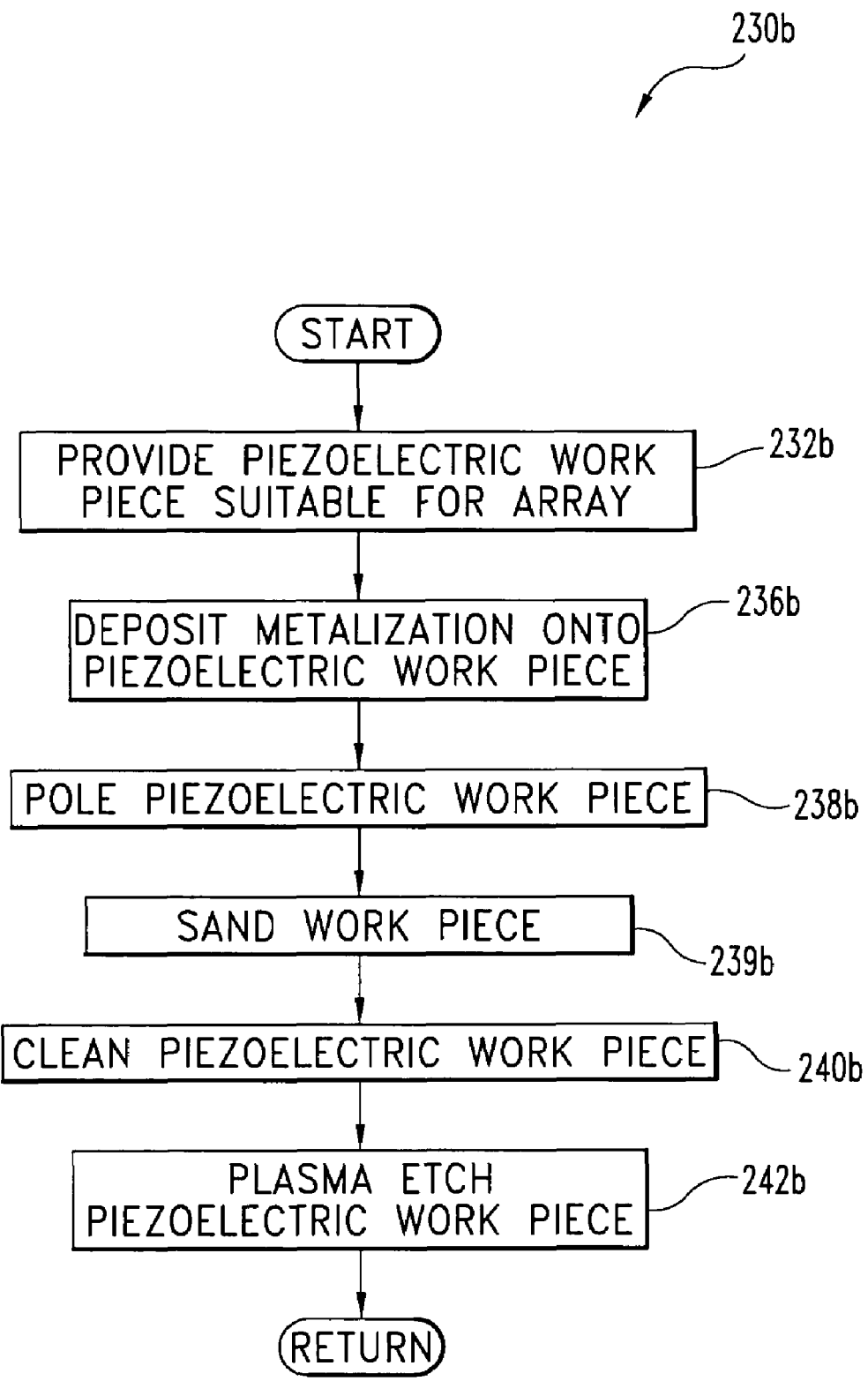
FIG. 9 is a flowchart illustrating the preparation of a piezoelectric member for the process of FIGS. 6 and 7.

Referring to the flowchart of FIG. 9, procedure 230b to prepare a piezoelectric component in accordance with operation 230 of process 220 is described. Procedure 230b begins with operation 232b. In operation 232a, a piezoelectric work piece is provided that is suitable for division into the elements 150 of array 150a. In one preferred form, this work piece is made of a piezoelectric material that includes one more types of lead-zirconium-titanium (PZT) ceramic. More preferably, a piezoelectric material is utilized that can be considered a combination of PZT and lead-magnesiumniobium (PMN) ceramics. In a preferred form, these piezoceramics are formed as a ceramic composition and not simply as a solid solution of two or more ceramic compositions or elements. Specific examples include ceramics of the formula: $Pb_{(1-z)}M_z(Mg_{1/3}Nb_{2/3})_x(Zr_yTi_{1-y})_{1-x}O_3$ where M is selected to be either Sr or Ba, and x is between about 0.1 and about 0.7, y is between about 0.25 and about 0.75, and z is between about 0.02 and about 0.1. A particularly preferred piezoceramic composition is represented by the following formula: $Pb_{0.94}Sr_{0.06}(Mg_{1/3}Nb_{2/3})_{0.375}(Zr_{0.392}Ti_{0.624})_{0.625}O_3$ or $Pb_{0.94}Sr_{0.06}Mg_{0.125}Nb_{0.250}Zr_{0.245}Ti_{0.39}O_3$.

In addition, such piezoceramics can include one or more dopant materials, which are not reflected in the above formula. Examples of dopants include manganese, niobium, tellurium, molybdenum, tantalum, and yttrium ceramics, more preferable the dopants include one or more of the following: $MnO_2$, $Ni_2O_3$, $TeO_2$, $MoO_3$, $Nb_2O_5$, $Ta_2O_5$, and $Y_2O_3$. In one preferred approach, one or more of the dopants are added to the piezoceramics in individual amounts up to about 2 weight percent (wt %), based upon the total weight of the piezoceramic. One preferred composition includes up to about 0.2 wt % $MnO_2$, based upon the total weight of the resulting ceramic. Another preferred composition includes up to about 1.6 wt % $Nb_2O_5$.

These piezoceramics can be prepared by slurrying the selected powdered metal oxides in a liquid such as water or an alcohol. The suspended powder is pulverized in a ball mill until the resulting mixed slurry is homogeneous and has a sufficiently small particle size. The resulting pulverized mixture is dried, preferably in an oven at elevated temperatures between about 100 and 150° C.

The resulting powder is thermally treated or calcined to form the desired perovskite structure. Preferably, the pulverized powder is heated to a temperature less than about 1000° C., more preferably to a temperature between about 900° C. to about 1000° C., still more preferably between about 925° C. and about 975° C. The powder is slowly heated to the selected temperature over a period of time. The heating rate can be varied considering the powder mass, the components in the powder, and the desired application for the final piezoceramic component. Preferably the powder is heated at a rate between about 100° C. and about 220° C. per hour, more preferably at a rate of between about 125° C. and 200° C. per hour, still more preferably at a rate of between about 150° C. and 190° C. per hour. Thereafter, the powder is held at that the high temperature for a time period. Again the hold time can be varied depending on the mass, identity and amount of the components in the powder. Typically the powder is held at the high temperature for a time period between about 1 and about 10 hours, more preferably between about 2 and about 6 hours. After this thermal treatment, the powder is allowed to cool back to room temperature.

The calcined powder is re-pulverized in a ball mill as has been described above, and then dried. This repulverized ceramic is then blended or suspended in a binder to provide a paste with the pulverized ceramic suspended in the paste. This paste is molded, pressed, or extruded as desired into a shaped article. The binder can be removed from the article either by heating to evaporate or burn-off the binder or, more preferably, by using a solvent to dissolve the binder material. The solvent can be any solvent, preferably an organic solvent into which the binder material exhibits a suitably high solubility. Typical solvents include alcohols, acetone, chloroform, methylene chloride, and other polar organic solvents which exhibit a relatively low boiling point or high vapor pressure.

The green article is then fired at elevated temperature range. The green article is placed in a suitable container such as an aluminum crucible and additional (unmolded) ceramic powder is placed around the shaped article during the firing process. The elevated temperature range can be selected to be between about 900° C. and about 1350° C., more preferably between about 950° C. and about 1300° C. The article can be held at a selected temperature in that temperature range for a time between about 10 and about 25 hours. More preferably, the article is slowly heated through the elevated temperature range at a selected heating rate. The heating rate can be selected by considering the mass or volume of the green article, the constituents in the ceramic and the desired properties of the piezoceramic article. After firing, the article can be cooled to ambient temperature.

For the purpose of promoting further understanding, the following example is provided; however, it should be understood that this example is merely illustrative and not limiting in any fashion. In this nonlimiting example, the following powdered ceramics were combined: PbO, 670.9 g; $ZrO_2$, 95.7; $TiO_2$, 96.1 g; $Nb_2O_5$, 121.0 g; MgO, 18.23 g; $SrCO_3$, 28.14; and $MnO_2$, 3.0 g. These powders were then suspended in 900 ml of deionized water and ball milled for about 16 hrs. The resulting powdered slurry was than dried at 130° C. The dried powder was calcined at 950° C. for 3 hours. Thereafter calcined ceramic powder was cooled to ambient temperature. The resulting ceramic was then re-pulverized by suspending in 1000 ml of deionized water and ball milling for 7 hrs. The pulverized ceramic was again dried at 130° C. to evaporate the water. The dried powder was suspended in a 5% polyvinyl alcohol (PVA) solution to provide a paste. This paste was extruded through a 1 7/16" slotted die under 1500 lb force to form a ceramic billet. This ceramic billet was fired at 1240° C. for 2.5 hours. Thereafter the ceramic billet was cooled to ambient temperature. Silver electrodes were patterned on the ceramic billet according to standard procedures. The resulting billet was then poled (polarized) at 115° C. and 70–80 V/mil for about 10 minutes.

In other embodiments one or more different procedures for making the piezoelectric material and/or one or more different piezoelectric compositions (such as PZT4, PZT8, a composite variety, a single crystal piezoelectric, and/or a piezoelectric polymer just to name a few nonlimiting examples) can be alternatively or additionally utilized for the work piece as would occur to those skilled in the art. Indeed, electrode deposition and poling are described differently than in the above-indicated example in connection with operations 236b and 238b hereinafter, to point out just a few other variations.

Figure 13:
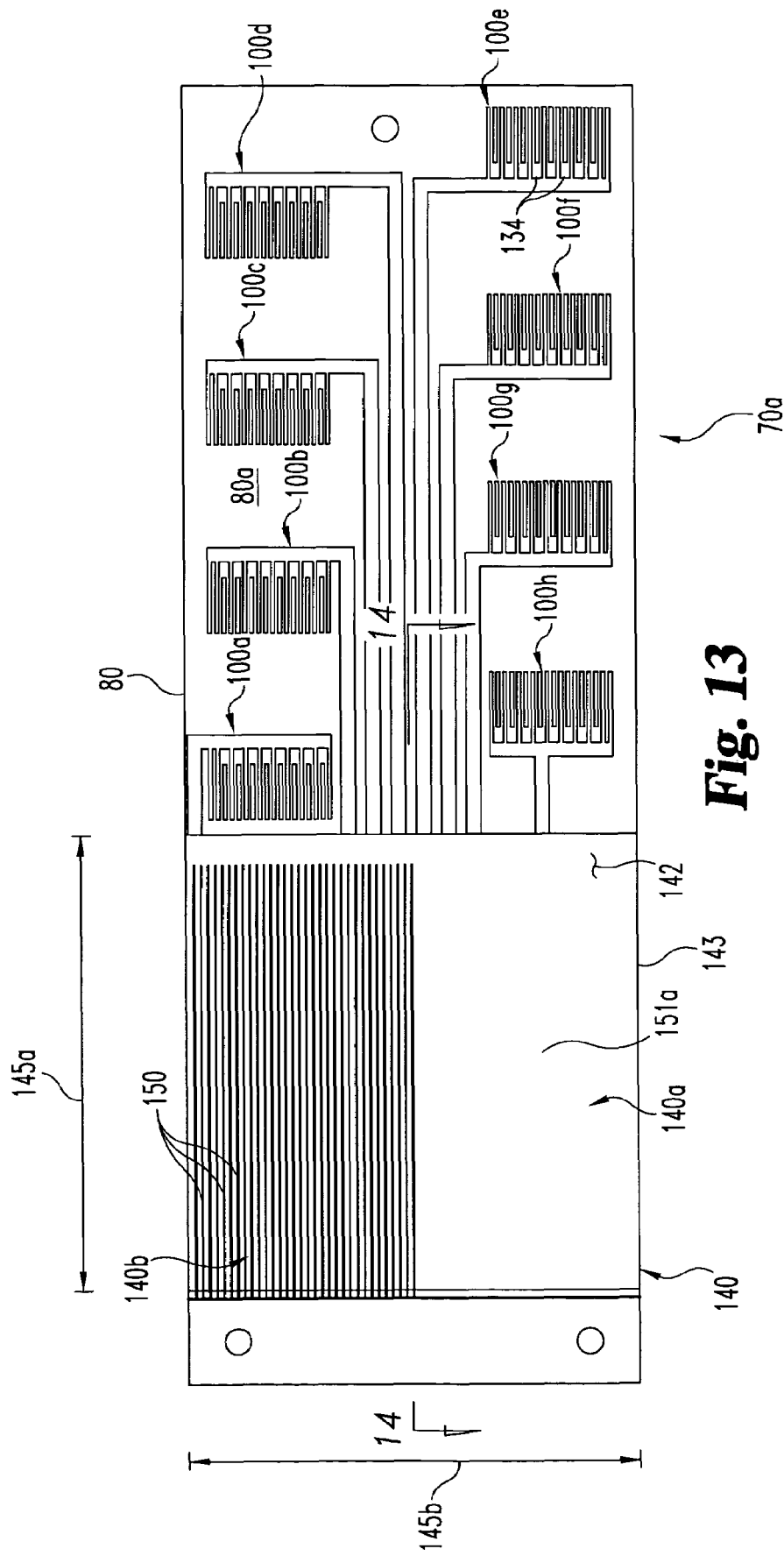
FIG. 13 shows a plan view of a partially assembled ablation device according to the process of FIGS. 6 and 7.
Figure 14:
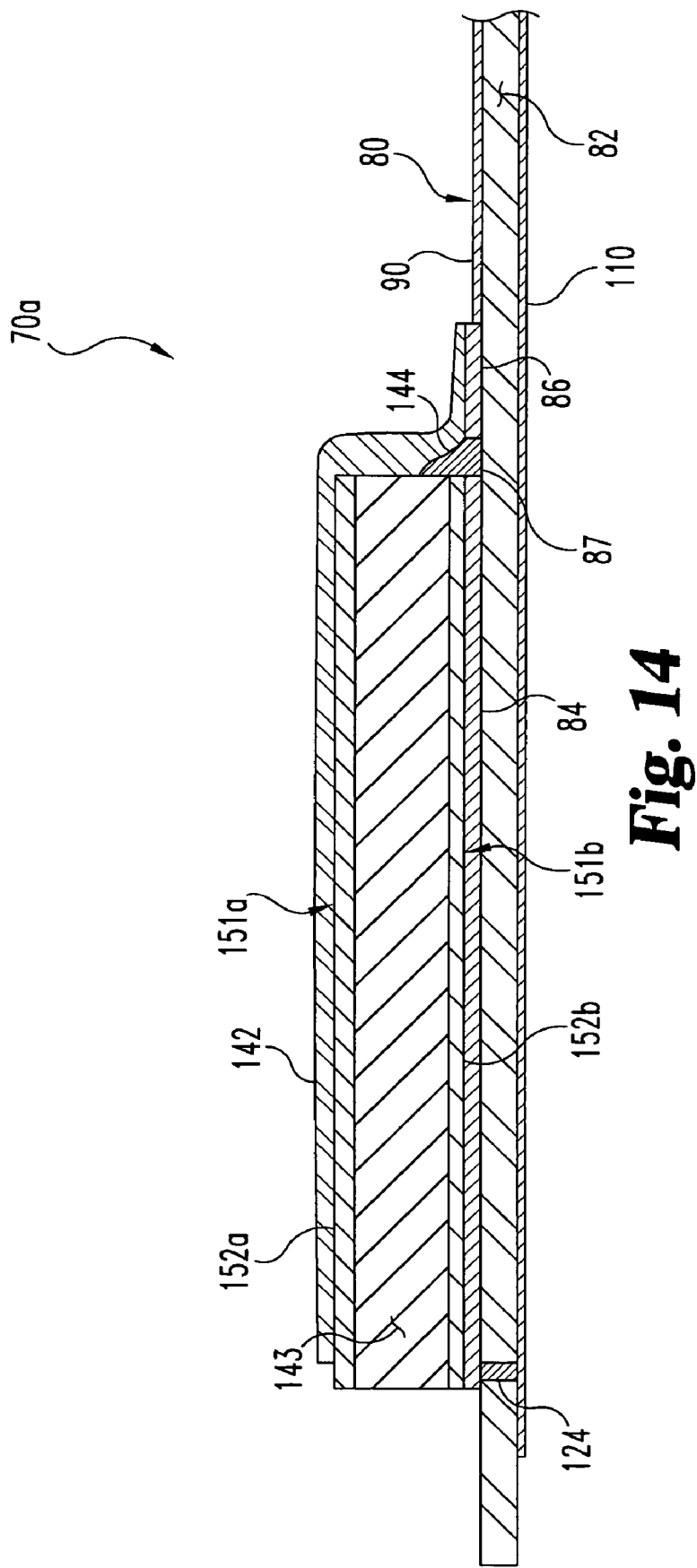
FIG. 14 is a partial, cross-sectional view of the partially assembled ablation device taken along section line 14—14 of FIG. 13.

The work piece for array 150a is generally shaped in the form of a parallelpiped block of piezoelectric material. The work piece includes two opposing faces sized and shaped generally the same as pad 84 of substrate 80 described in connection with FIG. 11. One of these faces is mounted to pad 84 in a subsequent operation of process 120 leaving the other exposed. FIGS. 13 and 14 illustrate partial assembly 70a corresponding to later operations of process 220. In partial assembly 70a, the piezoelectric work piece is mounted, being designated as mounted work piece 140. The two opposing faces previously described are designated by reference numerals 151a and 151b, respectively, in relation to mounted work piece 140.

Procedure 230b continues with operation 236b. In operation 236b, metallization is deposited on the opposing faces of the work piece to provide electrodes. FIG. 14 designates the resulting electrodes by reference numerals 152a and 152b in correspondence to faces 151a and 151b. In one form, the electrode metallization includes low temperature sputtering of gold or an alloy thereof; however, other deposition processes and/or materials suitable for electrode formation can be utilized in different embodiments.

Procedure 230b continues with operation 238b in which the piezoelectric material is poled (polarized). Polarization is provided by subjecting the work piece to: (a) a slow ramp-up to an elevated temperature, (b) a slow ramp-up of a polarizing electric field (voltage) across the electrodes while maintaining the elevated temperature, (c) a slow ramp-down to room temperature while the field is maintained, and (d) a slow ramp down of the electric field while at room temperature. Temperature changes are performed at a rate of about 1 degree C. per minute and voltage changes are gradual to a maximum of about 50–80 volts per mil thickness of material with a dwell time at maximum temperature and voltage of about 5 minutes. Performance parameters of the work piece are tested after poling. After parameter testing, the work piece edge that is designated for placement closest to pad edge 84a is sanded in operation 239b. After sanding, the work piece is cleaned in operation 240b with isopropyl alcohol and an ultrasonic cleaner. The work piece is also etched in a plasma-etching device in operation 242b. Procedure 230b then returns to process 220.

Returning to FIGS. 6 and 7, operation 230 of process 220 typically includes the preparation of other components to be described hereinafter. It should be understood that preparation of different components can typically be performed serially or in parallel and/or through an assembly-line or batch process. Process 220 proceeds from operation 230 to operation 250. In operation 250, the piezoelectric work piece is aligned for bonding to pad 84 by performing a visual inspection with a magnifying eyepiece to check position relative to features of side 80a of substrate 80. The edge sanded in operation 239b is lined-up with edge 84a during operation 250. The piezoelectric work piece is bonded to pad 84 of substrate 80 using high-strength adhesive and a clamp. Teflon fixtures on sides 80a and 80b of substrate 80 and the top of the piezoelectric work piece are used for the compression during bonding. Scribing of pad 84 in operation 236a of procedure 230a provides additional adhesive purchase for the secure bonding of each of elements 150 to substrate 80 as later formed from the work piece in a subsequent operation. Referring additionally to partial assembly 70a of FIG. 14, a portion 140a of mounted work piece 140 is illustrated. While the adhesive is not shown in FIG. 14 to preserve clarity, it is of a type that does not undesirably impede electrical connection between electrode 152b and pad 84, such as an epoxy with suspended carbon or metal particles, to name just one example. In other embodiments, a different adhesive or nonadhesive-based procedure can be used to couple the piezoelectric work piece to substrate 80.

From operation 250, process 220 continues with operation 252 in which the electrical connection of mounted work piece 140 is tested. After this testing, an electrically non-conductive bead of epoxy adhesive is place along the edge that was sanded in operation 234b of procedure 230b. The deposited epoxy bead is designated as nonconductive support member 144 in the sectional view of FIG. 14, and substantially occupies region 87. Member 144 is provided to reduce the likelihood of shorting between the bottom side (face 151b/electrode 152b) of the mounted work piece 140 and ground pad 86, and further provides a smooth transitional supporting structure between electrode 152a and ground pad 86 for formation of an electrical connection in a subsequent operation.

After member 144 has cured, the incomplete assembly is selectively masked, leaving only electrode 152a of face 151a, member 144, and ground pad 86 exposed in operation 256. The exposed area after masking corresponds to the rectangular region indicated by line segments 145a and 145b in relation to partial assembly 70a of FIG. 13; however, it should be understood that partial assembly 70a otherwise corresponds to a more advanced stage of manufacture. After masking in this manner, a layer of metallization 142 is deposited on the exposed region as illustrated in FIGS. 13 and 14. Accordingly, electrode 152a is electrically connected to ground pad 86 by metallization 142. In one form, this layer is formed by sputtering gold or an alloy thereof. In other forms a different electrically conductive material and/or deposition procedure can be utilized.

In operation 258, electrical connections are tested to verify proper electrical connectivity and isolation, as appropriate. Also, impedance is measured to verify proper electrical connection through the piezoelectric material of mounted work piece 140. From operation 258, process 220 continues with operation 262. In operation 262, mounted work piece 140 is divided into elements 150. In one form, separation of elements 150 is performed with a dicing saw. The dicing saw is aligned relative to the assembly using alignment trace 104 on side 80a of substrate 80 (the extra trace 104 is used to put the blade in the proper plane, and give the location for the first cut), and then used to cut the mounted work piece 140 into 64 equally sized elements 150. The blade of the saw cuts through metallization 142, piezoelectric body 143, at least a portion of member 144, electrodes 152a and 152b, bonding adhesive, pad 84, and at least 5 micrometers into substrate 80 to ensure complete electrical separation of elements 150 from one another and separation of pad 84 into corresponding pieces that are electrically isolated from one another. After separation, each element 150 includes a portion of electrode 151a electrically connected to metallization 142 and a portion of electrode 151b connected to a corresponding portion of pad 84 and via 124. Each of vias 124 is sized and positioned to provide electrically isolated interconnection to a different one of conductors 110 on side 80b of substrate 80 after performance of operation 262.

The partial assembly of FIGS. 13 and 14, corresponds to operation 262 after it has started, but before it is complete. As a result, a number of elements 150 have been separated in region 140b of FIG. 13, and separation of mounted work piece 140 into corresponding elements 150 has not been performed in region 140a. It should be appreciated that in other embodiments, a different separation technique (such as a laser cutting or selective etching to name just a few) may be alternatively or additionally utilized and/or some or all elements may be separated at substantially the same time, such that a partially separated state like that illustrated in FIGS. 13 and 14 would not typically result.

After operation 262, the assembly is tested in operation 264 to verify each of elements 150 is electrically connected to electrical ground at pads 86 and 92 through a portion of electrode 151a. Testing also verifies that each element 150 is electrically connected to a corresponding signal pad 102 through the electrical connection of corresponding portions of electrode 151b and pad 84, and a corresponding via 124, conductor 110, and via 120; and that signal pads 102 remain electrically isolated from each other and electrical ground. In this manner, side 80a predominantly defines traces for electrical ground and side 80b predominantly defines signal pathways.

Figure 10:
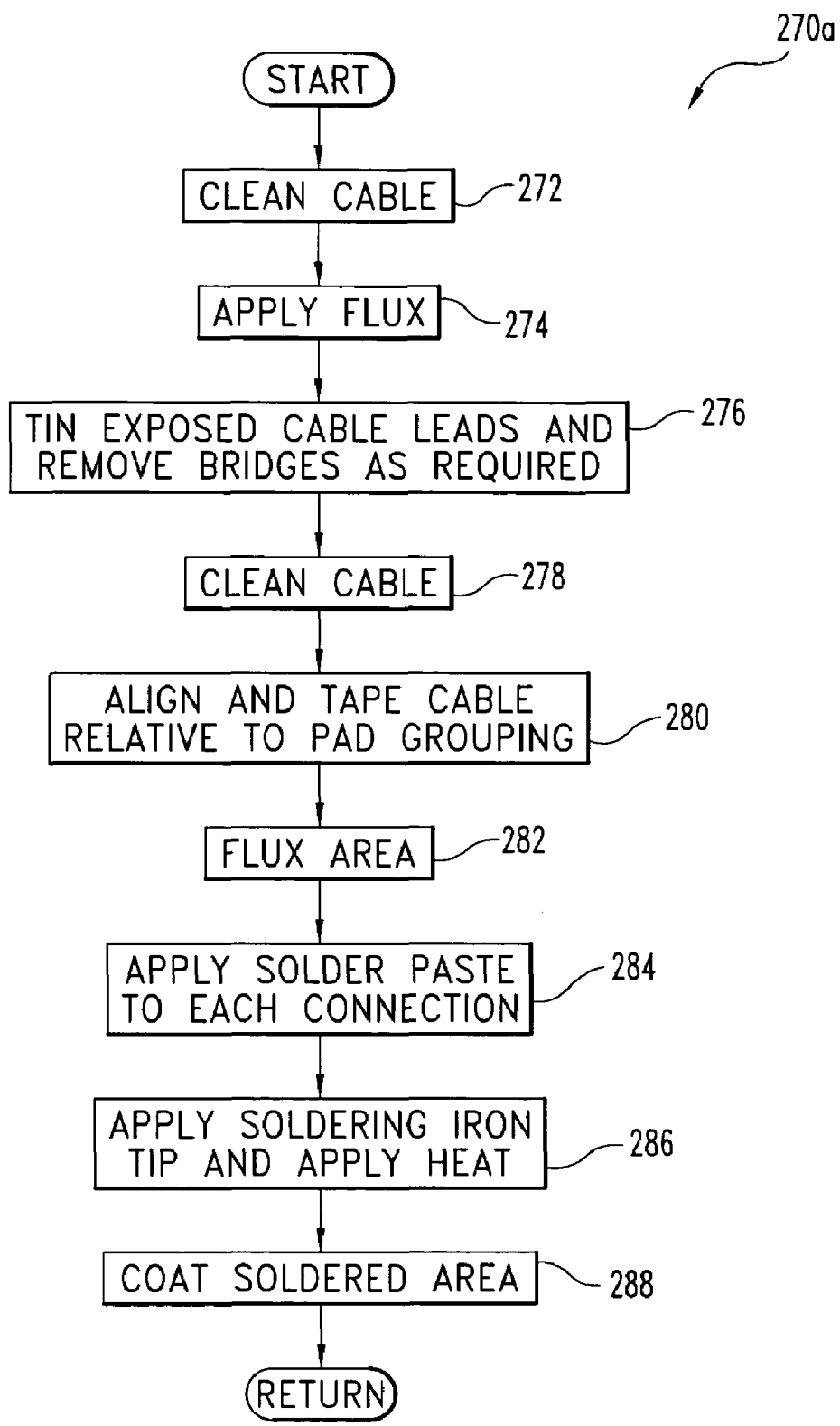
FIG. 10 is a flowchart illustrating a cable connection procedure for the process of FIGS. 6 and 7.
Figure 15:
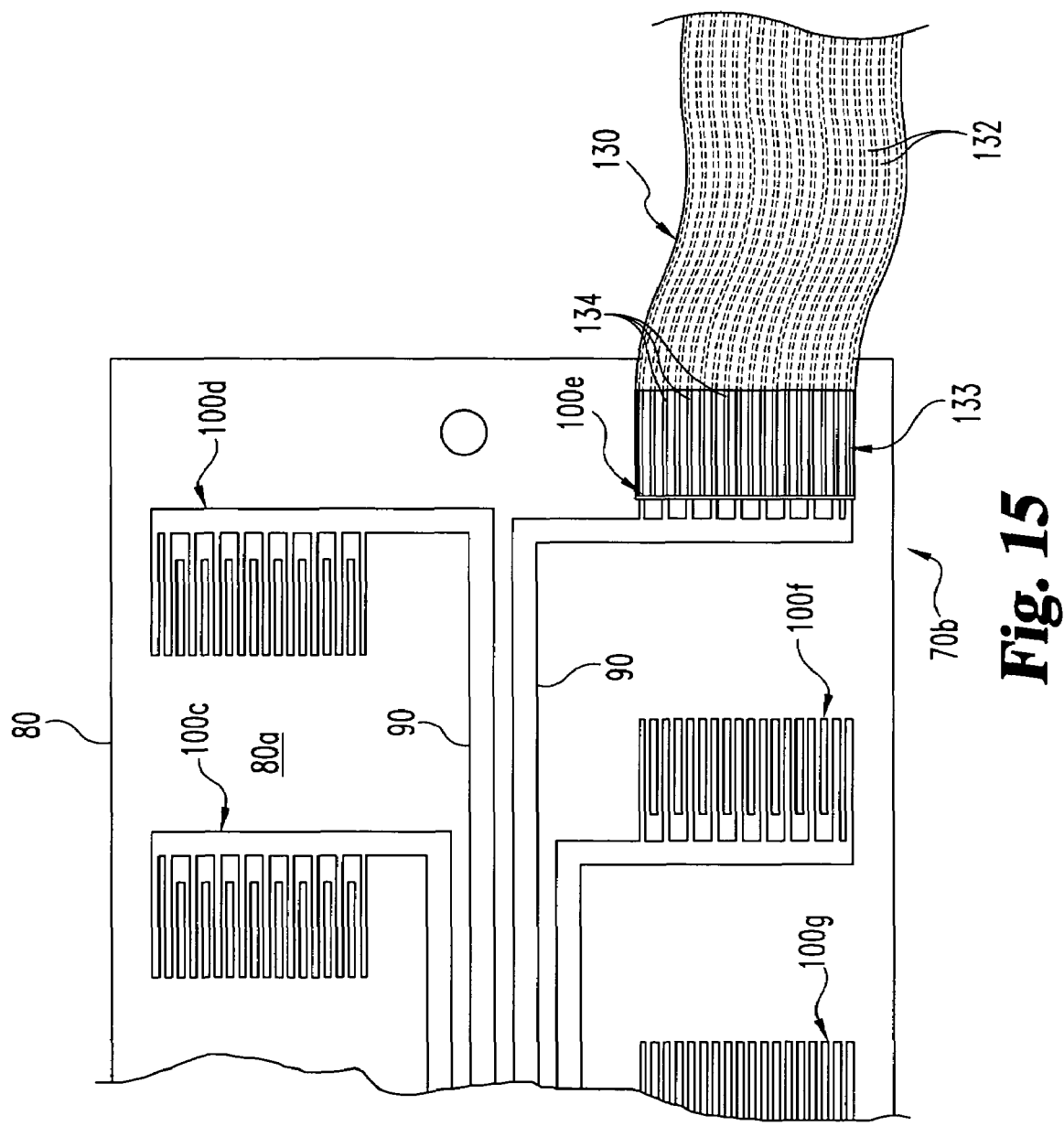
FIG. 15 is a partial assembly view of the ablation device during cable attachment in accordance with the process of FIGS. 6 and 7.

From operation 264 (FIG. 6), process 220 continues with cabling operation 270 (FIG. 7). In operation 270, eight multiple conductor cables 130 (FIG. 15) are connected to substrate 80 to provide cabling 162 (FIG. 1). Each cable 130 is coupled to a corresponding one of pad sets 100a–100h in accordance with procedure 270a described in connection with the flowchart of FIG. 10 and the partial assembly view of FIG. 15. The illustrated form of cable 130 is of a flexible ribbon type provided by W. L. Gore, in which conductors 132 are each in the form of 48 gage wire and are assembled between two organic polymer layers. Cable 130 includes eighteen conductors 132 terminating in a connection window region 133 where eighteen exposed contacts 134 are provided for connection to the eighteen pads (eight signal pads 102 and ten ground pads 92, see FIG. 11) of the corresponding one of pad sets 100. In the specific example of FIG. 15, cable 130 is connected to pad set 100e. In other embodiments a different number of cables, and/or a different type of wiring or cabling is used. In one particular alternative, a coaxial cable is used for each element.

In operation 272 of procedure 270a, region 133 is cleaned with isopropyl alcohol. In operation 274, flux is applied to contacts 134. In operation 276, contacts 134 are tinned by a rapidly dipping region 133 in a solder pot of molten Sn60Pb40 solder with a dwell time of less than one second. The solder pot temperature is maintained just a few degrees above the melting point for Sn60Pb40 solder. In other embodiments a different tinning and/or plating procedure can be utilized to accommodate the cable connection operation, or may be absent. After tinning, solder bridges between contacts 134 are removed with a heated small diameter soldering iron tip. Region 133 is cleaned in operation 278. In operation 180, cable 130 is aligned with substrate 80 and taped to substrate 80, registering each of contacts 134 with a respective pad 92 or 102 of the corresponding pad set 100 to which it is to be connected. In operation 282, flux is applied to region 133 and corresponding pads 92 and 102 (FIG. 11). Solder paste (SN62, less than 25 micrometer ball size) is then applied by placing 5–10 individual balls to each contact 134 and matching pad 92 or 102 in operation 284. In operation 286, a soldering iron is placed on the contact area that has a tip shaped to contact the matched contacts 134 and corresponding pad set 100 simultaneously. After placement, the soldering iron applies heat for about 2 seconds, and then it is turned off. Accordingly, contacts 134 of cable 130 are each soldered to a respective pad 92 or pad 102 of the given pad set 100. Any bridging is removed in operation 288 if required. Procedure 270a is performed for each of the pad set 100/cable 130 connections in operation 270 of process 220. The soldered region is then coated with a flexible potting material to protect the connections.

After operation 270, process 220 continues with operation 290. In operation 290, substrate/array assembly is placed in heat-shrink tubing. Heat is applied to the heat-shrink tubing to pre-form substrate 80 into a bent or rolled shape in operation 292. After cooling, the heat-shrink tubing is removed in operation 294. Next the preformed assembly is placed into a clamping fixture in operation 296. From operation 296, process 220 continues with operation 298 in which material 160 (FIG. 3) is applied to coat elements 150 and provide a filler therebetween. Also, member 170 is put in place during operation 298. The clamping fixture is slowly clamped, rolling the preformed assembly into a substantially cylindrical shape as previously described in connection with FIGS. 2–4 in operation 300. The assembly is cured while clamped, tip 72 is joined, and assembly 70 is provided, touching up as required in operation 302. Process 220 is then complete.

In other embodiments different ways of shaping, filling, and the like can be used. In still other embodiments one or more of material 160 and member 170 may not be used, and/or a longitudinal passageway through assembly 70 may be formed in member 170 and/or material 160 to receive a guide wire during use. For embodiments directed to ablation in the pulmonary vein region, process 220 can be utilized to provide 64 elements 150 in a unit that is about 6.4 millimeters wide before rolling with each element 150 having a size of about 85 micrometers by 6.5 millimeters, and still provide maximum individual acoustic power levels for each of the elements 150 on the order of one to two watts or more. After rolling or bending, assembly 70 can readily fit through a 7-French catheter. In this arrangement, a 3 millimeter heat shrink tubing is commonly employed for operation 292. In accordance with another embodiment of the present invention, ablation devices with multielement, high power arrays can be provided for catheter sizes in the 3–12 French range. In still other embodiments, some or all of process 220 is utilized to provide ultrasonic element arrays for other applications, including ablation for different procedures, tissue, or material types; ultrasonic sensing and/or imaging; or the like. Alternatively or additionally, the array assembly is formed into a noncylindrical shape or remains in the generally flat, noncylindrical shape shown in FIGS. 13–15, in which elements 150 are coplanar. In yet other embodiments, a process other than process 220 is used to manufacture ablation devices of the illustrated embodiments or variations of such devices as described herein.

All publications, patents, and patent applications cited in this specification are herein incorporated by reference as if each individual publication, patent, or patent application were specifically and individually indicated to be incorporated by reference and set forth in its entirety herein. Any theory, mechanism of operation, proof, or finding stated herein is meant to further enhance understanding of the present invention and is not intended to make the present invention in any way dependent upon such theory, mechanism of operation, proof, or finding. While the invention has been illustrated and described in detail in the drawings and foregoing description, the same is to be considered as illustrative and not restrictive in character, it being understood that only the selected embodiments have been shown and described and that all changes, modifications, and equivalents of the inventions as defined herein or by the following claims are desired to be protected.

What is claimed is:
1. A system, comprising:
an ablation device operable to be percutaneously placed within a patient's body, the ablation device including a proximal end portion, a distal end portion, and an array of ultrasonic ablation elements carried on a flexible substrate located at the distal end portion; wherein the flexible circuit substrate is formed in an approximately cylindrical shape with the elements positioned generally equidistant from a central longitudinal axis of the array; and wherein the elements are each elongate with a longitude generally parallel to said longitudinal axis; and
a control station coupled to the proximal end portion of the ablation device, the station including one or more processors operable to activate one or more elements of the array to selectively ablate tissue while the array is positioned within the patient's body.

2. The system of claim 1, wherein the one or more processors include operating logic to activate different groups of the elements in a selected sequence to correspondingly ablate different tissue regions.

3. The system of claim 1, wherein:
the array is generally formed in the shape of a cylinder with the elements being positioned approximately equidistant from a central longitudinal axis of the cylinder;
the control station includes one or more operator input devices; and
the control station is responsive to the one or more operator input devices to adjust focused ultrasonic energy provided by the array in relation to at least one of distance from the axis and angular position with respect to the axis.

4. The system of claim 1, wherein the elements number at least 32, the elements are each generally sized and shaped alike, and the elements are each comprised of a piezoelectric material.

5. The system of claim 4, wherein the elements number at least 64.

6. The system of claim 1, wherein the ablation device includes cabling with a number of electrical conductors electrically insulated from one another, the elements each being electrically connected to a different one of the conductors to receive independent activation signals from the control station.

7. The system of claim 1, wherein the station includes one or more operator input devices, a display, and analog circuitry operable to independently drive each of the elements in response to one or more signals from the one or more processors.

8. The system of claim 7, wherein the one or more processors are operable to provide a graphical output on the display corresponding to operating status of the ablation device.

9. A system, comprising:
an ablation device operable to be percutaneously placed within a patient's body, the ablation device including an array of at least eight ultrasonic tissue ablation elements located at a distal end portion of the device and cabling coupled to the array, the cabling extending to a proximal end portion of the device; wherein the ultrasonic tissue ablation elements are positioned in an approximately cylindrical shape with the elements positioned generally equidistant from a central longitudinal axis of the array; and wherein the elements are each elongate with a longitude generally parallel to said longitudinal axis; and
a control station coupled to the cabling, the station including one or more processors operable to activate different subsets of the elements in a desired sequence while the device is in the patient's body to correspondingly focus ultrasonic energy emanating from the device and to correspondingly ablate different segments of tissue circumferentially surrounding the device, the subsets each including two or more of the elements.

10. The system of claim 9, wherein the number of elements is at least thirty-two.

11. A system, comprising:
an ablation device operable to be percutaneously placed within a patient's body, the ablation device including an array of at least eight ultrasonic tissue ablation elements located at a distal end portion of the device and cabling coupled to the array, the cabling extending to a proximal end portion of the device and including a number of electrical conductors each electrically insulated from one another, the elements each being electrically connected to a different one of the conductors; wherein the ultrasonic tissue ablation elements are positioned in an approximately cylindrical shape with the elements positioned generally equidistant from a central longitudinal axis of the array; and wherein the elements are each elongate with a longitude generally parallel to said longitudinal axis; and
a control station coupled to the cabling, the station including one or more processors operable to independently activate the elements to selectively change focus of ultrasonic energy emanating from the device to ablate different tissue regions while the device is in the patient's body.

* * * * *